US009066824B2

(12) United States Patent  (10) Patent No.: US 9,066,824 B2
Madjarov  (45) Date of Patent: Jun. 30, 2015

(54) METHOD AND APPARATUS FOR ENDOVASCULAR THERAPY OF AORTIC PATHOLOGY

(71) Applicant: The Charlotte-Mecklenburg Hospital Authority, Charlotte, NC (US)

(72) Inventor: Jeko Metodiev Madjarov, Charlotte, NC (US)

(73) Assignee: The Charlotte-Mecklenburg Hospital Authority, Charlotte, NC (US)

(*) Notice: Subject to any disclaimer, the term of this patent is extended or adjusted under 35 U.S.C. 154(b) by 288 days.

(21) Appl. No.: 13/651,920

(22) Filed: Oct. 15, 2012

(65) Prior Publication Data

US 2013/0103132 A1    Apr. 25, 2013

Related U.S. Application Data

(60) Provisional application No. 61/550,066, filed on Oct. 21, 2011, provisional application No. 61/636,846, filed on Apr. 23, 2012.

(51) Int. Cl.
*A61F 2/07* (2013.01)
*A61F 2/95* (2013.01)
(Continued)

(52) U.S. Cl.
CPC ............... *A61F 2/852* (2013.01); *A61F 2/954* (2013.01); *A61F 2/06* (2013.01); *A61F 2002/061* (2013.01); *A61F 2250/0039* (2013.01); *A61F 2250/006* (2013.01)

(58) Field of Classification Search
CPC ............. A61F 2/06; A61F 2/82; A61F 2/067; A61F 2220/0025
USPC ................................. 623/1.11–1.38
See application file for complete search history.

(56) References Cited

U.S. PATENT DOCUMENTS 5,676,696 A * 10/1997 Marcade ..................... 623/1.35
5,984,955 A * 11/1999 Wisselink ..................... 623/1.35
(Continued)

FOREIGN PATENT DOCUMENTS

WO    WO 2006/028925 A1    3/2006
WO    WO 2011/064782 A2    6/2011

OTHER PUBLICATIONS

International Search Report and Written Opinion for Application No. PCT/US2012/061028 dated Feb. 5, 2013.
(Continued)

*Primary Examiner* — Suzette J Gherbi
(74) *Attorney, Agent, or Firm* — Alston & Bird LLP

(57) ABSTRACT

Assemblies, devices, and methods for positioning the same proximate a target site within a body lumen are provided. The assembly includes first and second components that can function independently of one another to address a patient's vascular abnormalities or can cooperate to form an assembly. The assembly is designed to address aortic pathologies near clusters of arterial branches in a way that allows blood to continue flowing to the arterial branches during the procedure while providing an adequate landing zone for the adjoining component. One of the components may include a tapered portion near one end that can be received by a corresponding end of the other component. Alternatively, one of the components may include an invaginated end that is able to receive a corresponding end of the other component such that the position of each component is substantially fixed with respect to the other.

22 Claims, 13 Drawing Sheets

(51) Int. Cl.
*A61F 2/852* (2013.01)
*A61F 2/954* (2013.01)
*A61F 2/06* (2013.01)

(56) References Cited

U.S. PATENT DOCUMENTS

| | | | | |
|---|---|---|---|---|
| 6,416,542 | B1* | 7/2002 | Marcade et al. | 623/1.16 |
| 6,524,336 | B1 | 2/2003 | Papazolgou et al. | |
| 6,652,580 | B1* | 11/2003 | Chuter et al. | 623/1.36 |
| 2006/0064159 | A1* | 3/2006 | Porter et al. | 623/1.24 |
| 2013/0041451 | A1* | 2/2013 | Patterson et al. | 623/1.12 |
| 2013/0123907 | A1* | 5/2013 | Roeder et al. | 623/1.23 |
| 2013/0274851 | A1* | 10/2013 | Kelly | 623/1.11 |
| 2014/0005765 | A1* | 1/2014 | Hamer et al. | 623/1.13 |

OTHER PUBLICATIONS

Chuter, Timothy A.M., et al.; "The Transition from Custom-Made to Standardized Multibranched Thoracoabdominal Aortic Stent Grafts";Journal of Vascular Surgery; vol. 54, No. 3; Copyright 2011 by the Society for Vascular Surgery; pp. 660-668.

Lioupis, C., et al.; "Treatment of Aortic Arch Aneuysms with a Modular Transfemoral Multibranched Stent Graft: Initial Experience"; European Journal of Vascular and Endovascular Surgery (2012); doi:10.1016/j.ejvs.2012.01.031.

El-Sayed, Hosam, et al.; "The Current Status of Endovascular Repair of Thoracic Aortic Aneurysms (TEVAR)"; Methodist DeBakey Cardiovascular Journal; vol. 7, No. 3; Jul.-Sep. 2011; pp. 15-19.

* cited by examiner

TO THE HEART

METHOD AND APPARATUS FOR ENDOVASCULAR THERAPY OF AORTIC PATHOLOGY

CROSS-REFERENCE TO RELATED APPLICATIONS

This application claims the benefit of U.S. Provisional Application No. 61/550,066 entitled "Method and Apparatus for Endovascular Repair of Aortic Pathology," filed Oct. 21, 2011, and U.S. Provisional Application No. 61/636,846 entitled "Method and Apparatus for Anatomical Endovascular Therapy of Aortic Pathology," filed Apr. 23, 2012, the contents of both of which are incorporated herein in their entirety.

FIELD OF THE INVENTION

The present invention relates generally to methods and apparatuses for endovascular therapy of aortic pathology. More specifically, methods and apparatuses are described for treating vascular abnormalities in the aorta near clusters of arterial branches, such as in the aortic arch proximate the innominate artery, the left carotid artery, and the left subclavian artery, as well as in the visceral segment of the aorta proximate the superior mesenteric artery (SMA), the celiac artery, and the renal arteries, where there may be limited space to provide an adequate landing zone for an endograft.

BACKGROUND

Vascular abnormalities can be serious medical conditions that require prompt and effective treatment. An aneurysm, for example, is a bulging or ballooning portion of the wall of a blood vessel, usually an artery, that is the result of a weakened area of the artery wall. As the aneurysm enlarges, the walls of the artery become thinner, and the risk of rupture increases. A ruptured aneurysm can cause severe hemorrhaging, other complications, and death. Weakened walls of the arteries can be hereditary or can be caused by disease, such as arteriosclerosis.

Conditions such as aneurysms can be treated by reinforcing the artery walls in the weakened areas. For example, vascular devices such as stents, grafts, and stent-grafts can be positioned within the artery proximate the abnormality to preclude blood flow from applying pressure on the damaged area of the vascular wall. Such devices may be delivered to the target site using surgical techniques; however, surgery is invasive and may present additional risks to the health of the patient, especially the elderly.

More recently, intravascular methods have been used to deliver medical devices without requiring surgery. In these cases, the stent-graft, for example, may be delivered to the target site via a delivery catheter that is advanced through the patient's vasculature to the area of the abnormality. The stent-graft, which is carried within the delivery catheter, may be deployed from a distal end of the delivery device and be expanded within the vasculature at the site of the abnormality.

Certain areas of the vasculature can be difficult to treat using traditional intravascular devices and methods. For example, portions of the aorta from which other arteries branch out and/or curved sections of the aorta may pose difficult challenges for the delivery, positioning, and maintaining-in-place of a vascular device.

Accordingly, there is a need for a method and apparatus for intravascularly treating aortic abnormalities in a way that is safe, reproducible, and simple to administer.

BRIEF SUMMARY

Assemblies, devices, and methods for treating a target site within a body lumen are thus provided. Embodiments of the assembly include first and second components that can function independently of one another to address a patient's vascular abnormalities or can cooperate to form an assembly. The assembly is designed to address aortic pathologies near clusters of arterial branches in a way that allows blood to continue flowing to the arterial branches during the procedure while providing an adequate landing zone for the adjoining component.

In one embodiment, a vascular assembly for treating a target site within a body lumen is provided that comprises a first component and a second component. The first component defines a first end, a second end, and a lumen extending therebetween, and the second component defines a first end, a second end, and a lumen extending therebetween. The second end of the second component may be configured to receive the second end of the first component. The first component may be configured to engage an inner surface of a vessel wall proximate a first group of arterial branches at the target site, and the second component may be configured to engage an inner surface of the vessel wall proximate a second group of arterial branches at the target site. Each of the first and second components may be independently deployable to the target site and may be configured for use at the target site both independently of the other component and in cooperation with the other component.

The second end of at least one of the first or second components may have a smaller inner diameter than the first end of the respective component, and at least a portion of the first and second components may be self-expandable. In some cases, at least one of the first and second components may comprise a tapered portion proximate the respective second end. The tapered portion and the respective second end may be balloon-expandable.

Alternatively or additionally, at least one of the first and second components may define at least one fenestration configured for extending a debranching limb into a corresponding arterial branch. Moreover, at least one of the first and second components may comprise at least one track defined by an inner wall of the respective component, where the track is configured to receive an end of the debranching limb.

An outer surface of the first end of the first component may be configured to engage an inner surface of a vessel wall proximate the target site, and an outer surface of the second end of the first component may be configured to engage an outer surface of the second component such that the second component is at least partially received within the first component and a position of the second component is substantially fixed with respect to the first component.

In some embodiments, the second end of the first component may comprise an inverted portion, such that an inner surface of an outer region of the second end of the first component faces an inner surface of an inner region of the second end of the first component in the inverted portion. The inverted portion may form an annular space, and the outer region of the second end may define at least one fenestration, such that blood flowing into the annular space is able to pass through the fenestration for maintaining blood flow to a branch vessel substantially aligned with the respective fenestration.

The assembly may be configured to be delivered intravascularly for treatment of a target site in the aortic arch, and/or the assembly may be configured to be delivered intravascularly for treatment of a target site in the visceral aorta.

In other embodiments, a vascular device for treating a target site within a body lumen is provided that comprises a first component defining a first end, a second end, and a lumen therebetween. An outer surface of the first end may be configured to engage an inner surface of a vessel wall proximate the target site, and an outer surface of the second end may be configured to engage an outer surface of a second component such that the second component is at least partially received within the first component and a position of the second component is substantially fixed with respect to the first component.

The second end of the first component may comprise an inverted portion, such that an inner surface of an outer region of the second end faces an inner surface of an inner region of the second end in the inverted portion. The inverted portion may form an annular space, and the outer region of the second end may define at least one fenestration, such that blood flowing into the annular space is able to pass through the fenestration for maintaining blood flow to a branch vessel substantially aligned with the respective fenestration.

In some cases, the first component may be configured to be located proximally to the heart with respect to the second component, whereas in other cases the first component may be configured to be located distally to the heart with respect to the second component.

In still other embodiments, a method for positioning a vascular assembly proximate a target site within a body lumen is provided. The method may comprise providing a vascular assembly including a first component comprising a first end and a second end and a second component comprising a first end and a second end. The second end of the first component may be configured to engage the second end of the second component. A first delivery device may be inserted into the body lumen, and a distal end of the first delivery device may be positioned proximate the target site. The first component may be advanced toward the target site via the first delivery device and then deployed from the first delivery device, such that the second end of the first component is positioned distally of at least one arterial branch and the first end of the first component is positioned proximally of the at least one arterial branch.

A second delivery device may be inserted into the body lumen, and a distal end of the second delivery device may be positioned proximate the target site. The second component may be advanced toward the target site via the second delivery device and deployed from the delivery device, such that the second end of the second component is positioned proximate the second end of the first component. The second end of the first component may be configured to cooperate with the second end of the second component such that a position of the first and second components with respect to each other and with respect to the target site is maintained.

In some cases, the second component may be deployed such that the second end of the second component receives the second end of the first component. At least one of the first and second components may comprise a tapered portion proximate the respective second end, where the tapered portion defines at least one fenestration for alignment with at least one arterial branch such that a debranching limb may be inserted through the at least one fenestration and into the at least one arterial branch. The second ends of the first and second components may be engaged via balloon-expansion following deployment of the second component such that the second end of the second component receives the second end of the first component.

In some embodiments, the second end of the first component may comprise an inverted portion, such that an inner surface of an outer region of the second end faces an inner surface of an inner region of the second end in the inverted portion. The second component may be deployed such that the second component is at least partially received within the first component via the inverted portion of the second end of the first component.

BRIEF DESCRIPTION OF THE DRAWINGS

Figure 1:
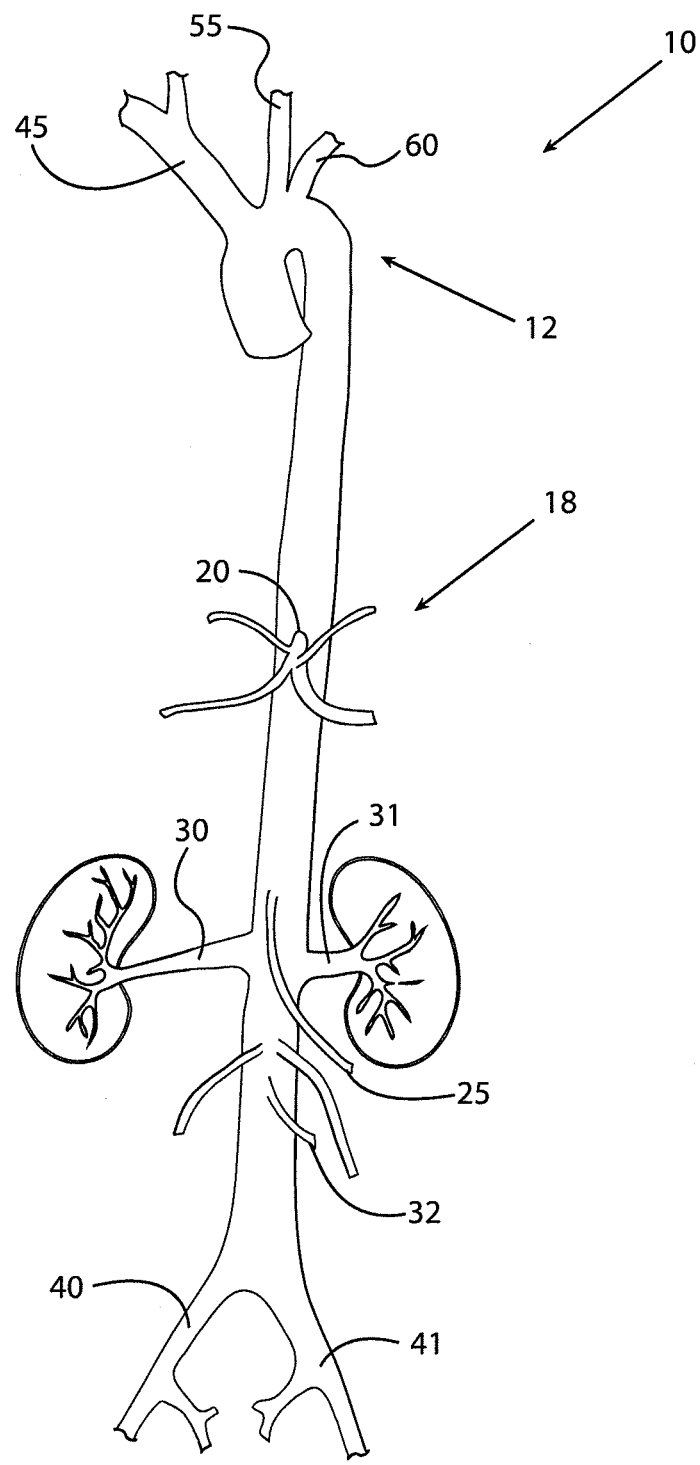
Figure 2:
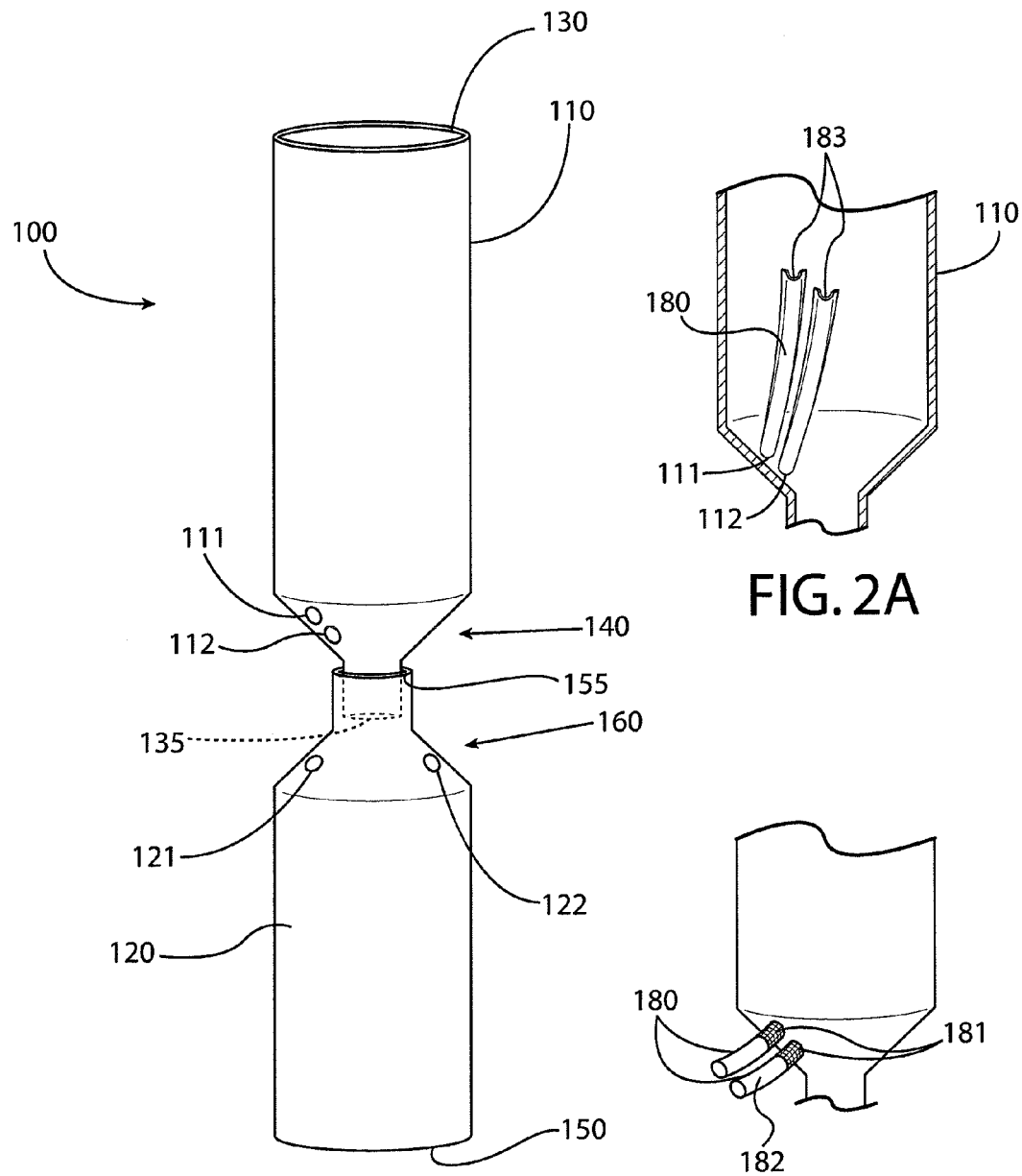
Figure 3:
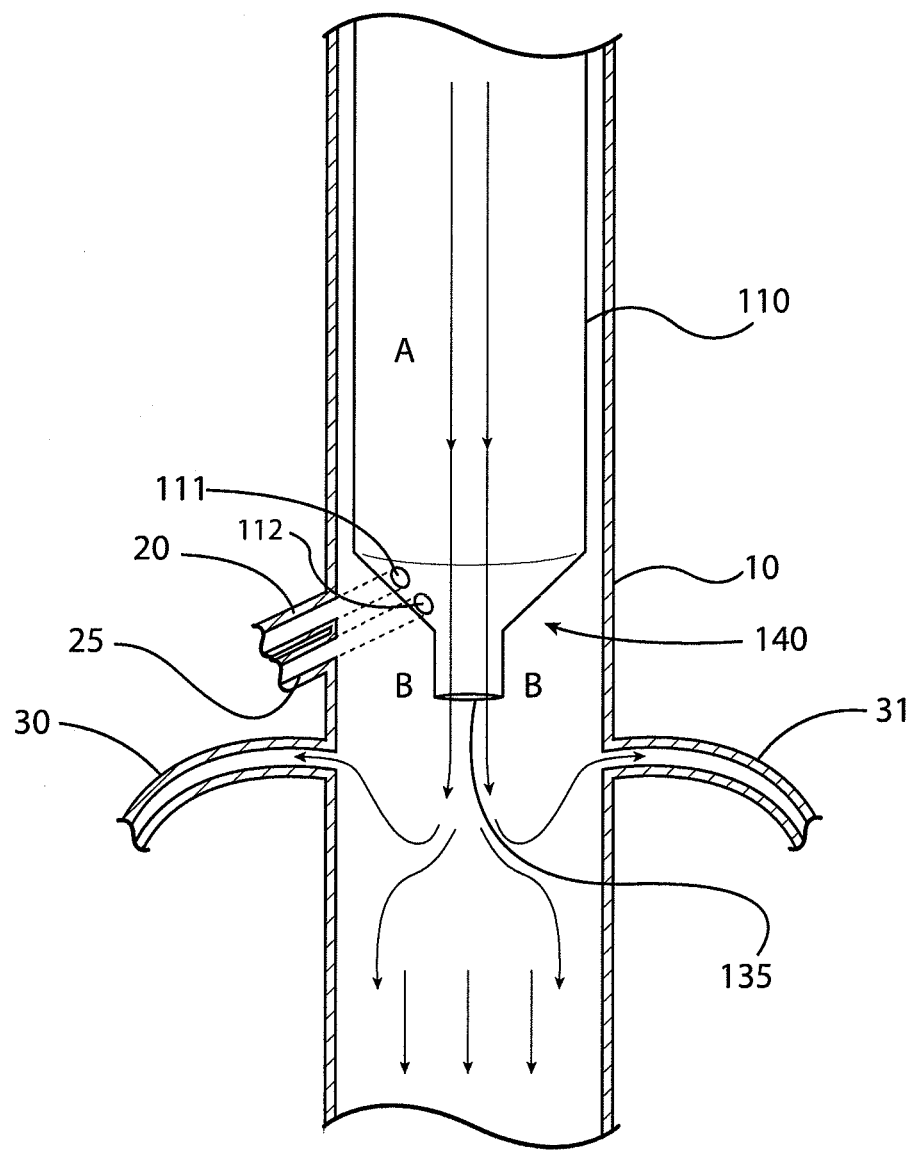
Figure 4:
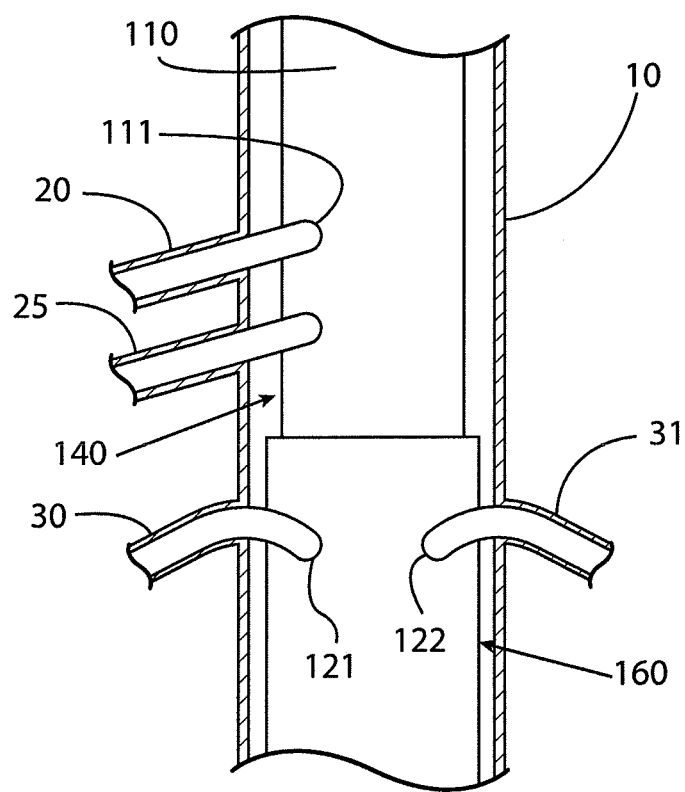
Figure 5:
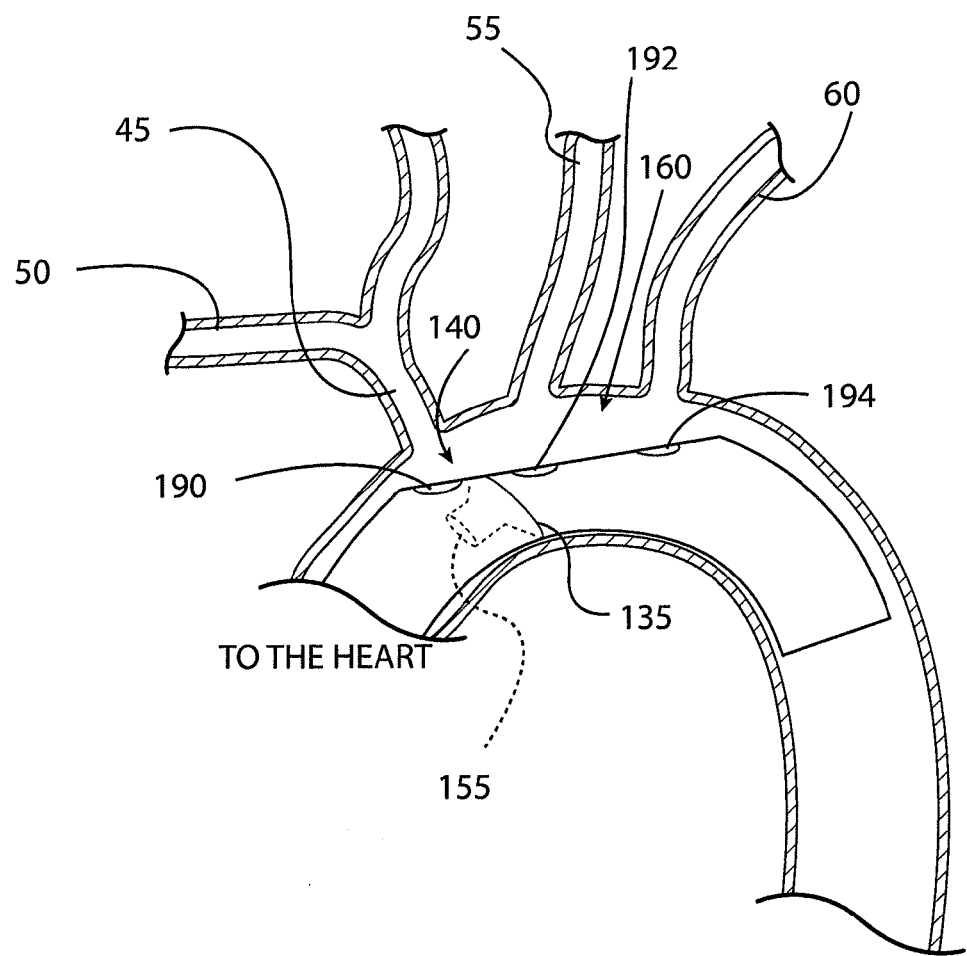
Figure 6A:
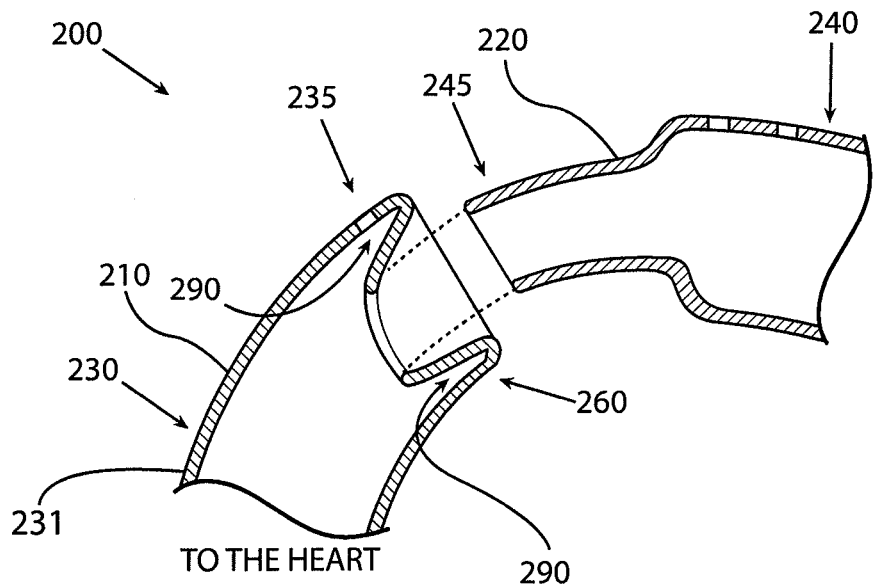
Figure 6B:
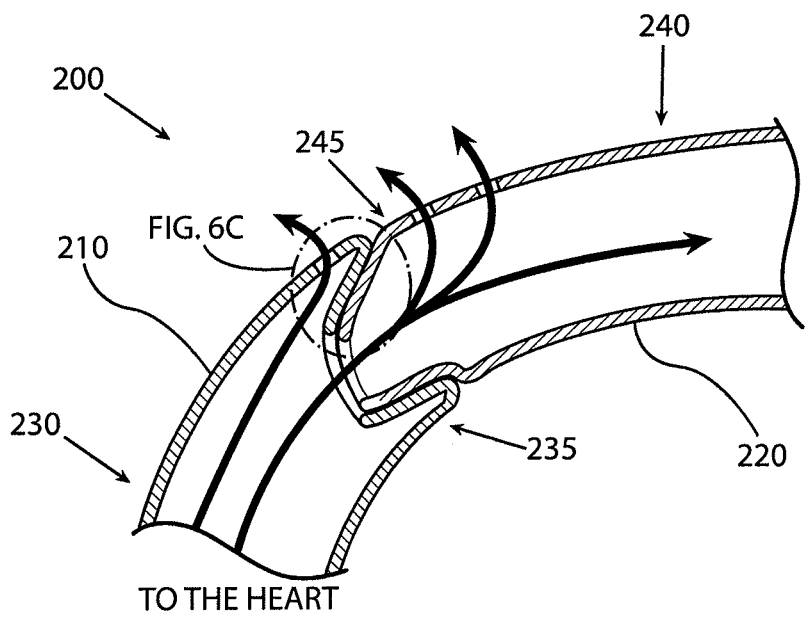
Figure 6C:
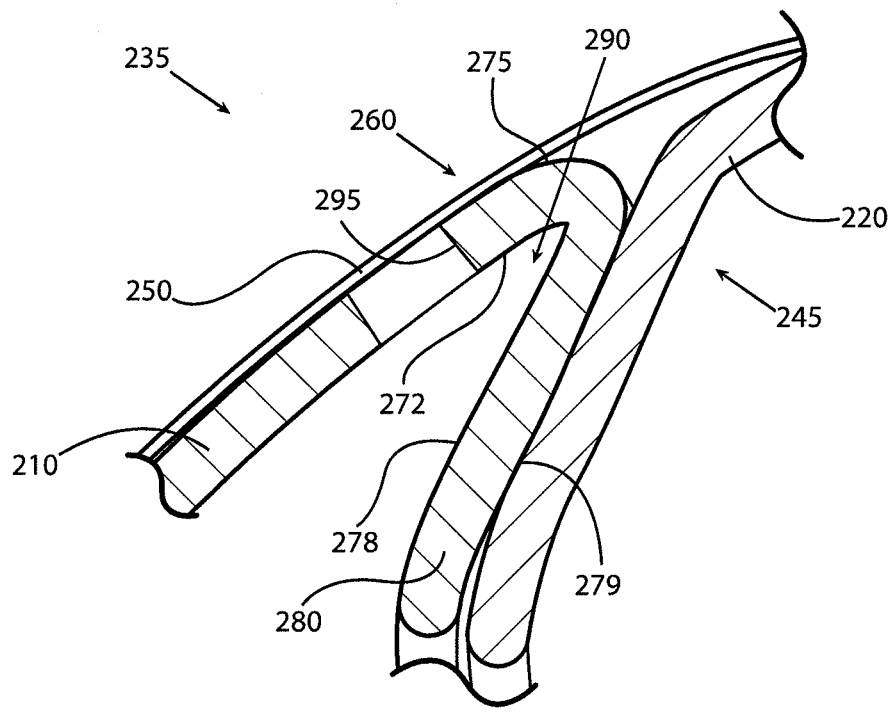
Figure 6D:
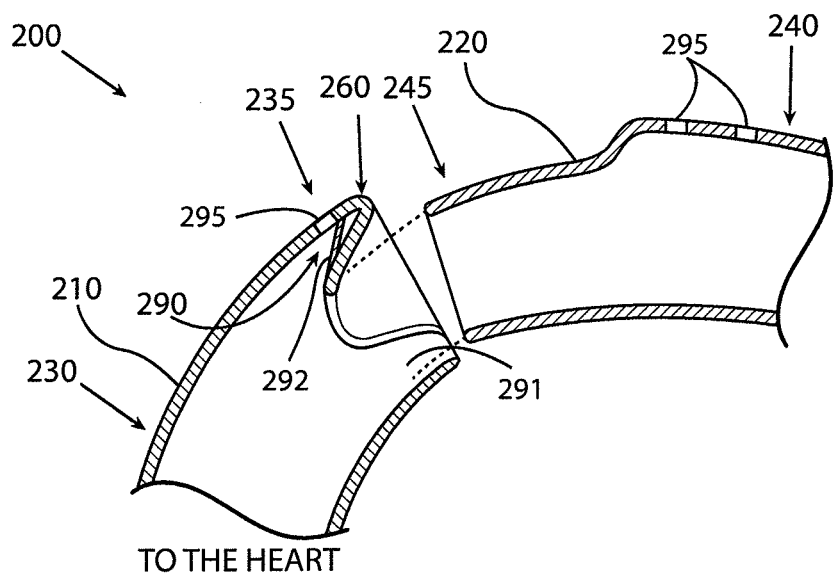
Figure 7:
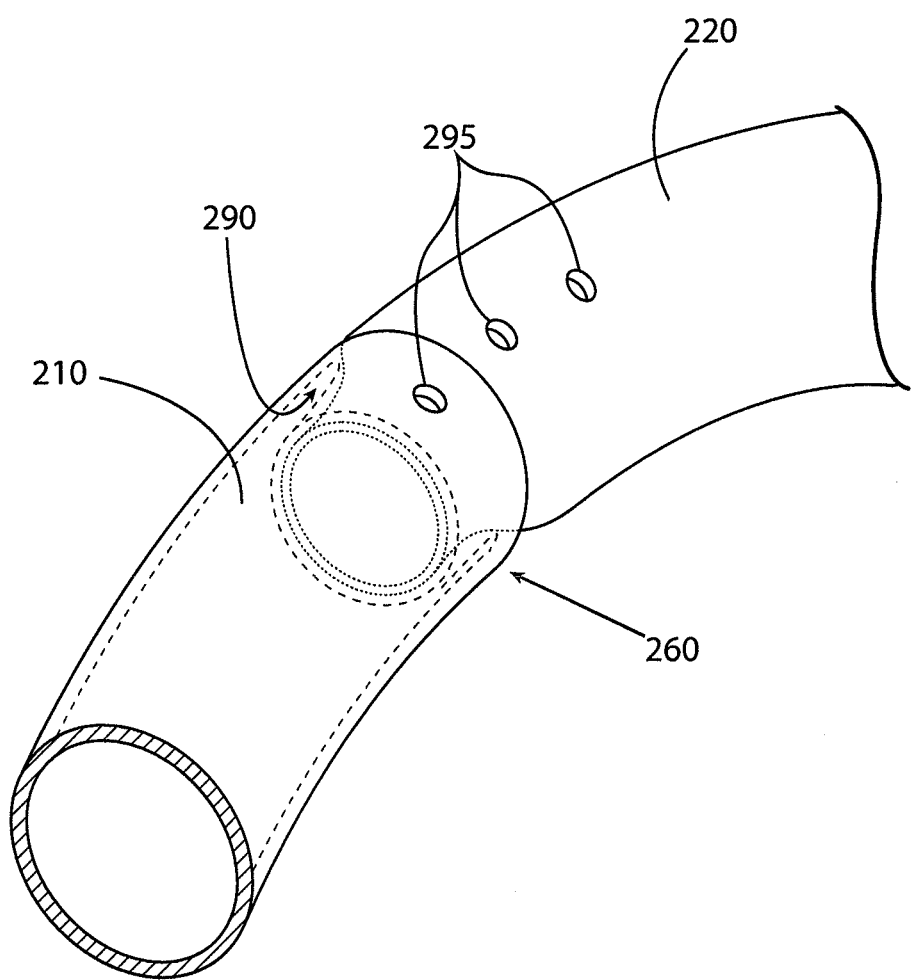
Figure 8A:
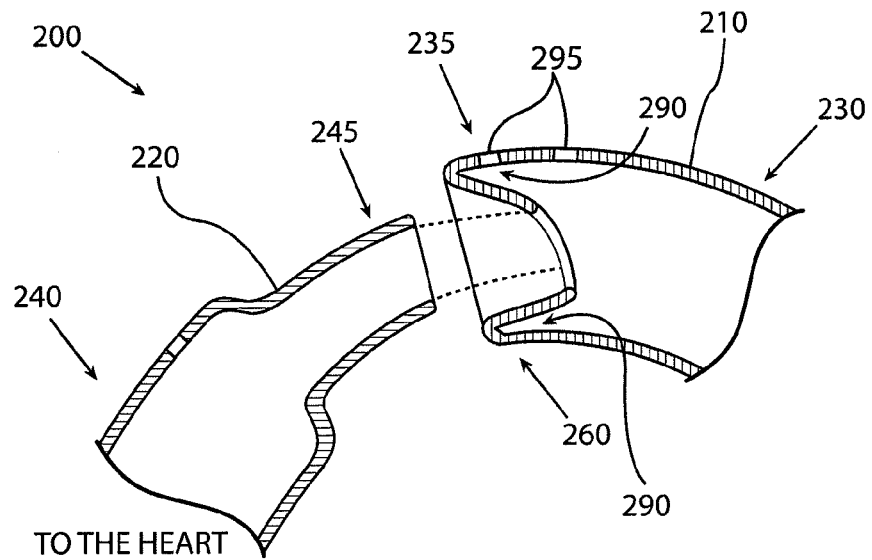
Figure 8B:
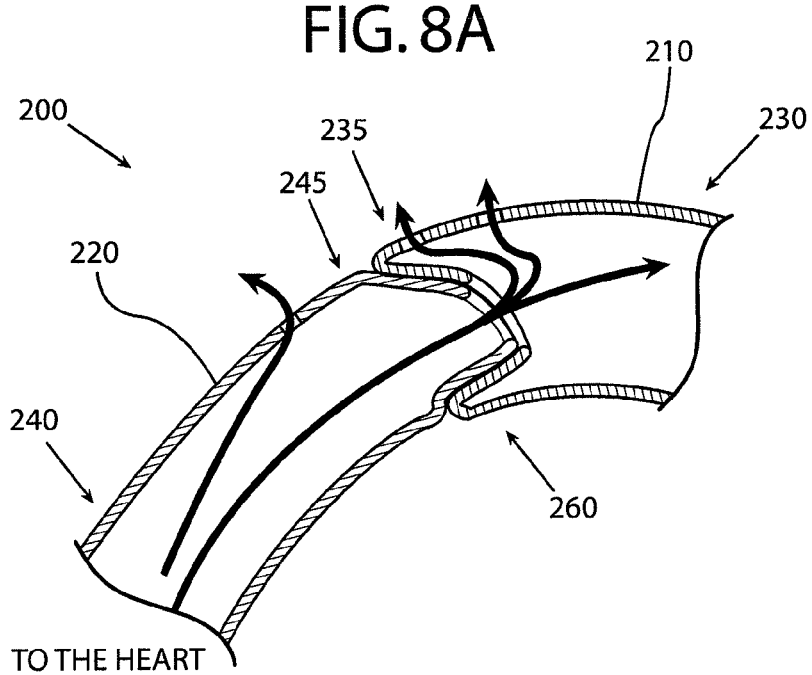
Figure 9:
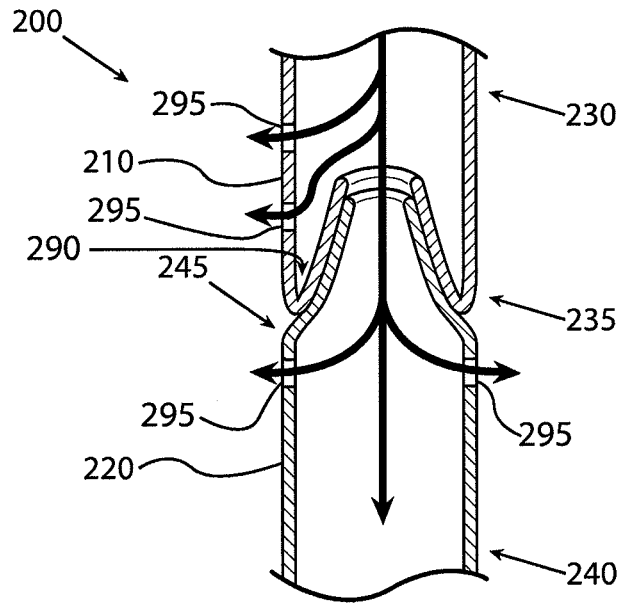
Figure 10:
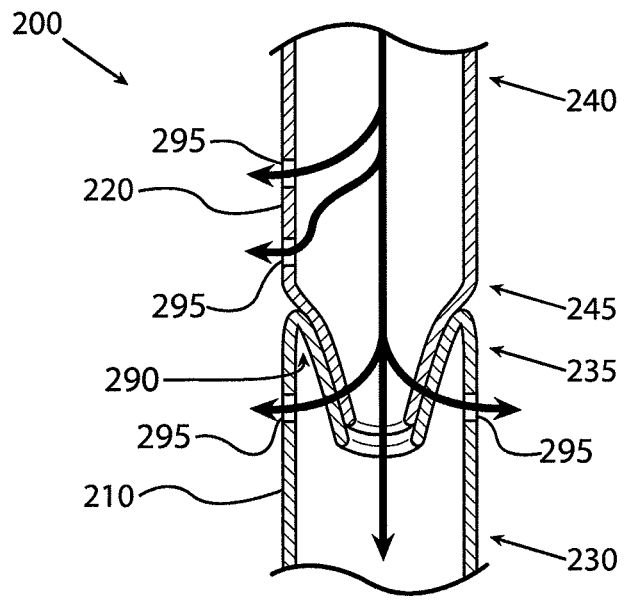
Figure 11:
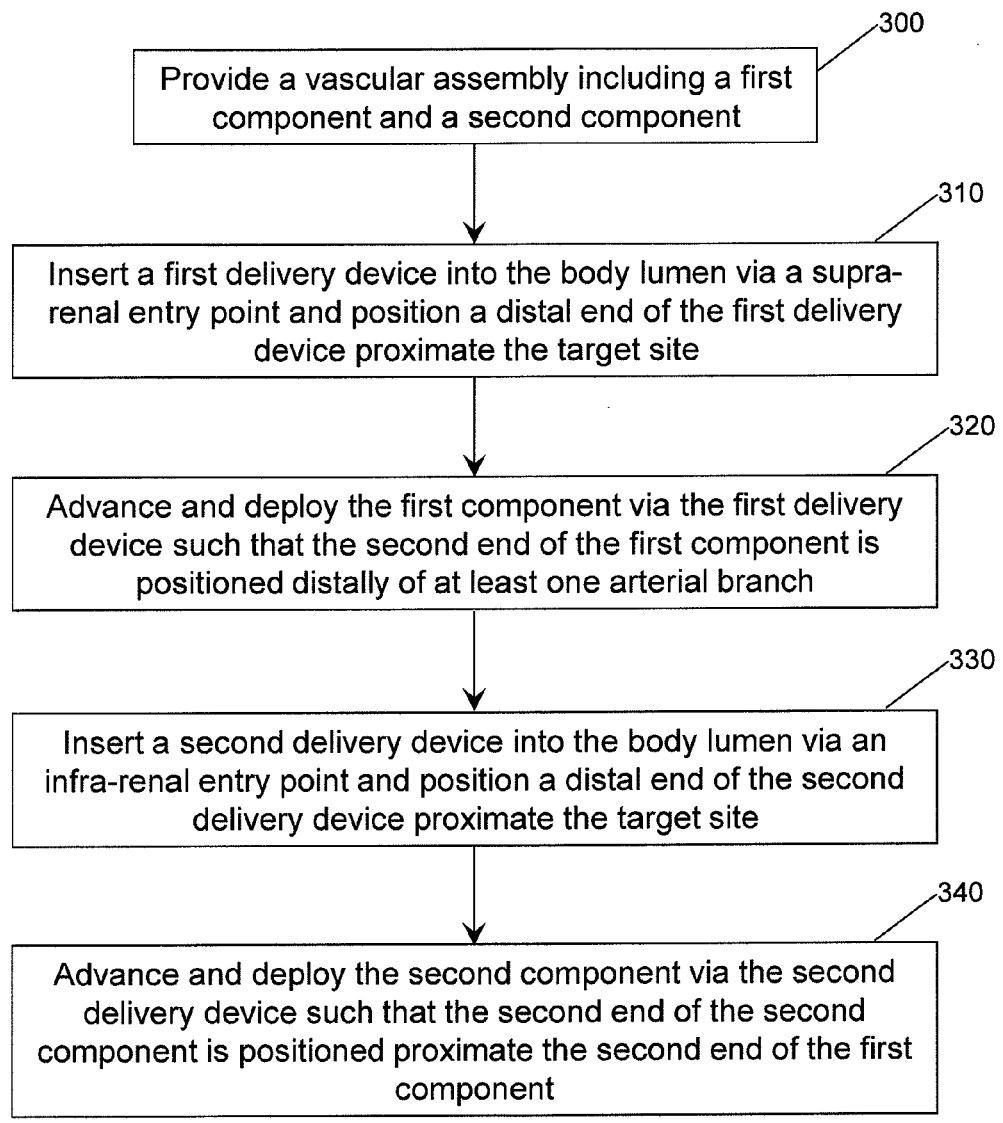
Figure 12:
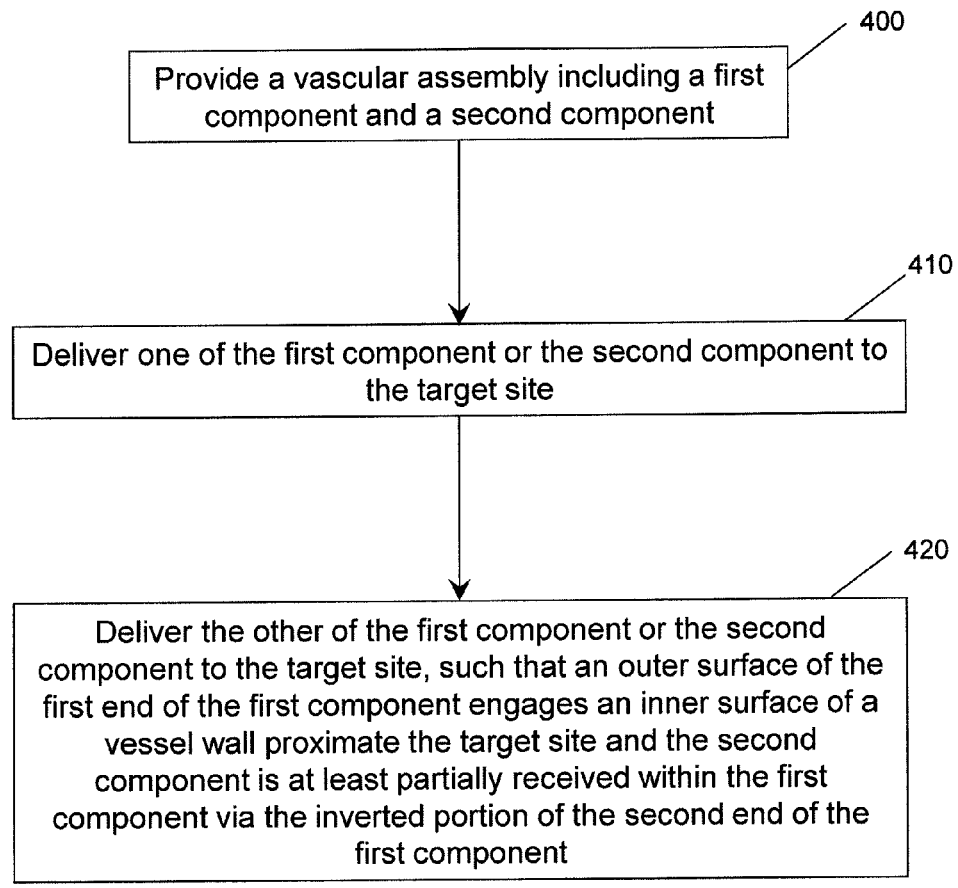
Figure 13:
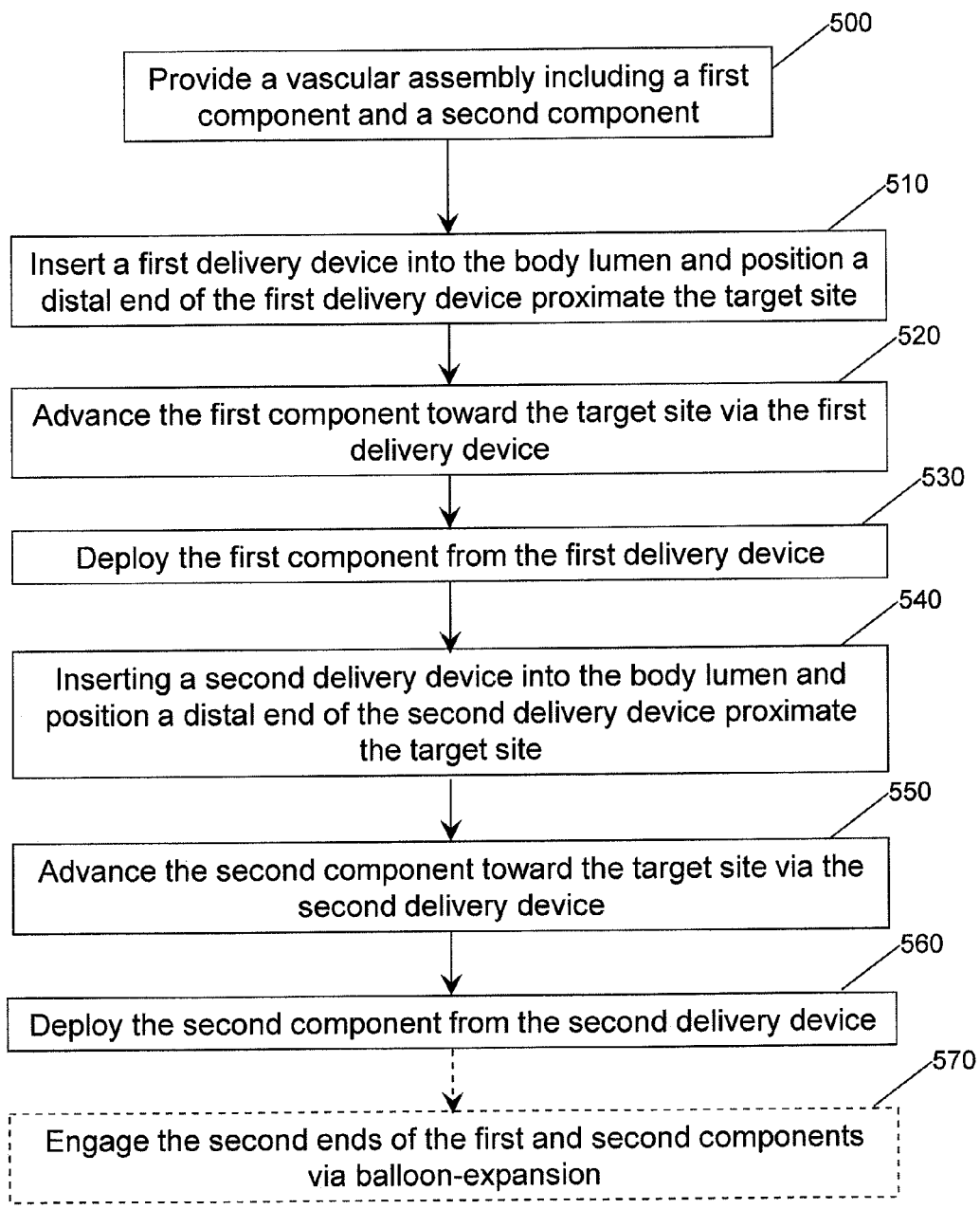

Having thus described the invention in general terms, reference will now be made to the accompanying drawings, which are not necessarily drawn to scale, and wherein:

FIG. 1 shows a schematic representation of an aorta with arterial branches;

FIG. 2 shows a schematic representation of a vascular assembly including a first component and a second component and debranching limbs configured for intra-vascular delivery to a target site proximate the celiac artery, the SMA, and the renal arteries in accordance with an exemplary embodiment of the present invention;

FIG. 2A shows a perspective view of an inner wall of the first component showing a track in the inner wall for guiding a debranching stent-graft to a fenestration;

FIG. 2B shows a perspective view of an outer wall of the first component of FIG. 2A showing an extension of the track;

FIG. 3 shows a schematic representation of the first component of the vascular assembly of FIG. 2 upon delivery to the target site in accordance with an exemplary embodiment of the present invention;

FIG. 4 shows a schematic representation of the first and second components of the vascular assembly of FIG. 2 after the distal ends of the components have been engaged with each other in accordance with an exemplary embodiment of the present invention;

FIG. 5 shows a schematic representation of a first component and a second component of a vascular assembly for addressing a pathology in the aortic arch prior to full engagement of the respective second ends in accordance with an exemplary embodiment of the present invention;

FIG. 6A shows a schematic cross-sectional representation of a vascular assembly in expanded form including a first component and a second component configured for intravascular delivery to a target site in the aortic arch in accordance with another exemplary embodiment of the present invention;

FIG. 6B shows a schematic cross-sectional representation of the vascular assembly of FIG. 6A in assembled form in accordance with an exemplary embodiment of the present invention;

FIG. 6C shows a schematic cross-sectional close up view of the engagement of the first and second components of FIG. 6B in accordance with an exemplary embodiment of the present invention;

FIG. 6D shows a schematic cross-sectional representation of a vascular assembly in expanded form including a first component having a support structure for the annular space in accordance with another exemplary embodiment of the present invention;

FIG. 7 illustrates a perspective cross-sectional representation of the first and second components of the vascular assembly of FIG. 6A in accordance with an exemplary embodiment of the present invention;

FIG. 8A shows a schematic cross-sectional representation of a vascular assembly in expanded form including a first component and a second component configured for intravascular delivery to a target site in the aortic arch in accordance with another exemplary embodiment of the present invention;

FIG. 8B shows a schematic cross-sectional representation of the vascular assembly of FIG. 8A in assembled form in accordance with another exemplary embodiment of the present invention;

FIG. 9 shows a schematic cross-sectional representation of a vascular assembly in assembled form including a first component and a second component configured for intravascular delivery to a target site in the visceral aorta in accordance with an exemplary embodiment of the present invention;

FIG. 10 shows a schematic cross-sectional representation of a vascular assembly in assembled form including a first component and a second component configured for intravascular delivery to a target site in the visceral aorta in accordance with another exemplary embodiment of the present invention; and FIGS. 11-13 illustrate flowcharts of methods for positioning a vascular assembly proximate a target site within a body lumen in accordance with exemplary embodiments of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" refer to a location farthest from a reference point, such as the heart; the terms "proximal" and "proximally" refer to a location closest to the reference point. Furthermore, although the examples described herein refer to aneurysms in the ascending aorta and the aortic arch and/or the abdominal aorta, embodiments of the described invention may be used to treat various vascular abnormalities, including aneurysms, type A dissections, and type B acute dissections, in various locations, including the ascending aorta, the aortic arch, the thoracic aorta, and other blood vessels.

Referring now to FIG. 1, a schematic representation of an aorta 10 is shown. Thoracoabdominal aortic pathologies are often considered some of the most difficult aortic pathologies to treat. The ascending aorta and the aortic arch 12, for example, are sections that include a high degree of curvature, as well as arteries that branch up to feed oxygenated blood to the head, neck, and arms. Such arteries include the innominate artery 45, the left common carotid artery 55, and the left subclavian artery 16.

The abdominal aorta 18, which begins at the diaphragm, also includes several important arterial branches that feed most of the major organs. Such arteries include the celiac artery 20, the superior mesenteric artery (SMA) 25, the renal arteries 30, 31, the inferior mesenteric artery (IMA) 32, and the femoral arteries 40, 41. Aortic abnormalities, such as aneurysms and dissections (e.g., a tear in the inner wall of the aorta that creates a false lumen between the layers of the wall of the aorta), can be extremely difficult to treat when they occur in sections of the aorta that include a number of arterial branches, such as in the aortic arch and the abdominal aorta, for example. This is because conventional vascular devices, such as endografts and stents, require a section of vasculature proximal to and distal from the respective ends of the device to serve as "landing zones," or lengths of native vessel that engage portions of the vascular device and keep the device in position at the target site. Typically, landing zones of approximately 2 cm are required.

In the location of clusters of arterial branches, such as in the aortic arch proximate the innominate artery 45, the left common carotid artery 55, and the left subclavian artery 60, and in the visceral aorta proximate the celiac artery, SMA, and renal arteries, however, there is no 2 cm-section of aorta available to act as a landing zone due to the high density of arterial branches. Moreover, the fact that there is a cluster of arterial branches complicates the use of conventional vascular devices, as blockage of these branch arteries by the vascular device blocks or restricts blood flow to the parts of the body being fed by these arteries.

Conventional solutions have attempted to address these problems in different ways. For aortic aneurysms located proximate the celiac artery and SMA, for example, fenestrated endografts have been used that are delivered to the abdominal aorta from an infra-renal entry point in the vasculature. The fenestrations, or openings in the walls of the endografts, which are typically custom-made by the surgeon for the particular patient, must be carefully aligned with the branching arteries to ensure that adequate blood flow is provided to the downstream organs. Even when the fenestrations are properly aligned, however, the natural expansion and contraction of the aorta with each heartbeat often causes the migration of the stent-graft over time. As a result of such migration, the initial alignment of the fenestrations may be lost, and the organs fed by the affected artery may suffer the consequences of inadequate blood flow.

For relatively small aortic aneurysms located in the aortic arch, as another example, the fenestrated endograft may be intravascularly delivered to the aorta from an entry point in the vasculature that is distal from the heart, such as in the descending aorta. The fenestrations must again be carefully aligned with the branching arteries to ensure that adequate blood flow is provided to the downstream organs, and again the natural expansion and contraction of the aorta with each heartbeat often causes the migration of the stent-graft over time, disturbing the initial alignment of the fenestrations and potentially reducing the amount of blood flow to the downstream organs.

In other cases, branched endografts (e.g., an endograft having smaller-diameter stent-grafts extending therefrom) may be used to deploy additional "branches" of a main stent-graft into the arterial branches. Such methods provide structural support to the arteries, in addition to maintaining a passage for the blood flow from the main portion of the endograft. As with fenestrated endografts, however, branched endografts are conventionally delivered to the target site from a distal entry point in the vasculature. Due to the angle of arterial branches with respect to the aorta, however, it is often difficult to extend the debranching stent-graft limbs from the main endograft into the arterial branch. For example, with respect to the visceral aorta, branched endografts are conventionally delivered to the target site from an infra-renal entry point in the vasculature. The angle of arterial branches such as the celiac artery and the SMA with respect to the aorta thus make it difficult to extend the debranching stent-graft limbs from the main endograft into the respective arterial branch. Furthermore, migration of the endograft (i.e., in the direction of the patient's feet) or aortic remodeling may create stresses at the juncture of the main endograft with the stent-graft limbs. Thus, over time, fractures may occur, which could allow blood to enter the area of the aneurysm.

For larger aneurysms in the aortic arch in particular, surgery may be required to repair the site of the abnormality by cutting out the damaged section of the aorta and replacing that section with a prosthetic graft. Such devices may include debranching limbs (e.g., smaller-diameter stent-grafts that are extended from a main endograft) that attempt to reflect the size and spacing of the arterial branches, such that each limb may be inserted into a respective arterial branch for maintaining blood flow to downstream parts of the body. As noted above with respect to branched endografts, because the size of patients requiring these treatments varies, and because the anatomy of each patient is unique, these devices often fail to properly correspond to the particular patient's anatomy and, thus, the use of such devices may place additional stresses on the patient's vasculature and the graft itself due to improper sizing and/or differences between the angles at which the limbs join to the vascular device and the natural angles of the arterial branches with respect to the aortic arch.

Accordingly, embodiments of the present invention provide for a two-component vascular assembly for addressing aortic pathologies. As shown and described in greater detail below, the end of one of the components may be configured to be received by the end of the other component such that the two components may be delivered to and deployed at the target site separately from each other, but at the same time may cooperate and act as one device once in position within the body lumen. Moreover, each of the components may be configured to function independently of the other, such that if only a certain portion of the aorta requires repair, only one of the components need be deployed. If, at a later time, the adjacent section of the aorta also requires repair, the second component may be deployed and joined to the first component to complete the two-component device and more fully address the aortic abnormality. In some embodiments, the adjoining ends of the components comprise a single tubular cross-section, as shown in FIGS. 2-5, whereas in other embodiments the end of one of the components is invaginated, or folded inward onto itself, to create a second, narrower-diameter tubular cross-section configured to receive the respective end of the adjoining component, as shown in FIGS. 6A-10. In both cases, a landing zone is created within an end of one of the components for receiving the adjoining end of the other component, as described in greater detail below.

With reference to FIG. 2, a vascular assembly 100 is thus provided that comprises a first component 110 and a second component 120. As noted above, although the first and second components 110, 120 are separate from each other for purposes of delivery and deployment at the target site, the two components are configured to cooperate and act as one device once in position within the body lumen. Alternatively, each component 110, 120 may be used independently of the other, as will be described in greater detail below.

Using a repair of the visceral aorta as an example, the first component 110 may be configured to be delivered to the target site via a delivery device that is positioned within the body lumen from either a supra-renal entry point or an infra-renal entry point (e.g., an opening of the vasculature by the practitioner). Examples of supra-renal entry points may include locations in the axillary arteries, the brachial arteries, or the subclavian arteries. Examples of infra-renal entry points include femoral arteries. Thus, in some cases, ante-grade delivery (i.e., delivery in the direction of blood flow) may be used to position the first component and/or the second component proximate the target site. In other cases, retrograde delivery (i.e., delivery in a direction opposite the direction of blood flow) may be used to position one or both components. The delivery device (e.g., the delivery catheter) may, for example, be a 16-20 Fr device.

In this regard, the first component 110 may include a first end 130 and a second end 135. The second end 135 may have a smaller diameter than the first end 130; thus, a tapered portion 140 may be provided proximate the second end 135. In some cases, the first component 110 may be delivered to the target site in a radially constrained state (e.g., via a delivery catheter), such that the diameter of the first component is held in a reduced, compact configuration by the walls of the delivery device. The first component 110, or at least portions of the first component, may be self-expandable, such that once the radial constraint is removed, the first component achieves a pre-defined larger diameter.

Thus, in some embodiments, once the first component 110 has been deployed from the respective delivery device, and, for example, the first component 110 is allowed to self-expand towards an unconstrained state at the target site, the tapered portion 140 and the second end 135 may maintain a smaller diameter with respect to portions of the first component proximate the first end 130. For example, the first end 130 may have a diameter of approximately 30 mm-48 mm (e.g., in 2 mm increments), whereas the tapered portion and/or second end 135 may have a diameter of approximately 16 mm-30 mm (e.g., in 2 mm increments). In this way, with reference to FIG. 3, the first component 110 may be positioned in a location near the renal arteries 30, 31 without impeding the flow of blood to the kidneys. Rather, blood flowing in the direction A in FIG. 3 would flow past the narrow-diameter portion and back up (in the direction B) to the renal arteries.

Fenestrations 111, 112 may be defined in the tapered portion 140 for receiving debranching stent-graft limbs for insertion into branching arteries, such as the celiac artery and SMA, via the first component 110. With reference to FIG. 2A, which shows the inner wall of a portion of the first component 110, tracks 180 may be provided along the inner wall of the first component for guiding stent-graft limbs along at least a portion of the length of the first component, out through the fenestrations 111, 112, and into the aligned celiac artery and SMA (in this example). The tracks 180 may be configured as cylindrical tubes formed within (e.g., molded as part of) or otherwise attached to the inner wall of the first component 110 within which at least a portion of the stent-graft limbs may extend. Each of the tracks 180 may be approximately 4 mm-10 mm in diameter and may extend approximately 1.5-2.5 cm along the inner wall of the first component 110.

In some embodiments, the tracks 180 may comprise a fabric (e.g., Gore-tex® or Dacron® material) or metal mesh sleeve (or a combination thereof) that is attached to the inner wall of the first component 110. A marker band 183 (shown in FIG. 2A) made of a radiopaque material may be provided at an end of each track 180 most distal from the respective opening 111, 112 to maintain access to the lumen of the track (e.g., to keep the track open), as well as to provide the surgeon with a visual indication of the location of the opening of the track to facilitate the insertion of the guidewire and/or stent-graft limb into the track.

In addition, in some embodiments, a portion of the track 180 may extend out of the respective opening 111, 112 so as to guide the stent-graft limb into the corresponding branch artery. For example, with reference to FIG. 2B, a first portion 181 of the track 180, which may be fabric only, may extend out of the opening 111, 112, followed by a second portion 182 of the track made of fabric supported by mesh, where the second portion of the track is configured to extend at least partially into the corresponding arterial branch. The first portion 181 may be approximately 1 mm-2 mm long, and the second portion 182 may be approximately 4 mm-6 mm long.

By providing a 1 mm-2 mm section of fabric only between the inner portion of the track 180 and the portion of the track that is configured to extend into the arterial branch, the track may be allowed to bend and flex somewhat, e.g., to enable better alignment with the corresponding arterial branch and to prevent kinking or damage to the component during delivery and/or deployment, as well as following the procedure (e.g., due to aortic remodeling).

The first component 110 and the stent-graft limbs (shown via dashed lines in FIG. 3) may each be delivered over guidewires. Once the main endograft is in position proximate the target site, the debranching limbs may be extended through the fenestrations 111, 112 and expanded into the respective arterial branches.

The provision of tracks 180, through which the guidewires may pass for delivering the stent-graft limbs, can encourage a more natural angle for delivery of the stent-graft limbs. In other words, by passing the stent-graft limbs through the tracks 180 via the guidewires, the angle of the stent-graft limbs at the juncture with the wall of the first component 110 may be held fixed at an angle that minimizes the stresses on the stent-graft limbs and/or the first component. Furthermore, the tracks 180 may serve as "landing zones" for the respective stent-graft limbs, thereby reducing the risk of migration of the stent-graft limbs with respect to the main endograft. As noted above, each track 180 may be configured to have a diameter that approximates the diameter of the branching arteries into which the tracks are configured to guide the debranching limbs (e.g., the celiac artery and the SMA). In addition, in cases where debranching limbs (e.g., for support of the celiac artery and/or SMA) are not needed, plugs (not shown) may be inserted into one or both of the tracks 180 to prevent blood from escaping via the fenestrations 111, 112.

The configuration (i.e., size and shape) of the tapered portion 140 and the second end 135 of the first component 110 allows blood to flow into the renal arteries in this example, as described above and illustrated in FIG. 3. Because blood flow is maintained to the renal arteries, proper positioning of the first component 110 and any debranching limbs through the fenestrations 111, 112 may take place without raising undue concern about blood flow to the kidneys. In other words, the practitioner may take more time to properly position the first component 110 and any debranching limbs without significantly affecting blood flow to the patient's kidneys.

Once the first component 110 is in place, referring back to FIG. 2, the second component 120 may be delivered to the target site (if necessary) by a delivery device (which may be the same as or different from the delivery device for the first component) that is inserted into the patient's vasculature.

The second component 120 may include a first end 150 and a second end 155, with respect to the entry point. The second end 155 may, in some cases, have substantially the same diameter as the first end 150. In other cases, though, the second end 155 of the second component 120 may have a smaller diameter than the first end 150 and may include a tapered portion 160, as depicted. The diameter of the second end 155 of the second component 120, however, may be larger than the diameter of the adjacent second end 135 of the first portion 110. As such, the second end 135 of the first component 110 may be configured to be received within the second end 155 of the second component 120, as described in greater detail below. For example, the first end 150 of the second component 120 may have a diameter of approximately 22 mm-40 mm, and the second end 155 of the second component may have a diameter of approximately 18 mm-30 mm.

As with the first component 110, debranching limbs may be extended from the main endograft of the second component 120, through fenestrations 121, 122, and into the renal arteries to allow for more direct blood flow to the kidneys and support of the renal arteries. As noted above with respect to the first component 110, tracks (not shown) may be provided in the inner wall of the second component 120 to guide the debranching limbs out through the fenestrations 121, 122 and into the corresponding renal arteries.

Finally, after the first and second components 110, 120 are in place, the second ends 135, 155 of the respective components may be connected, joined, affixed or otherwise engaged to each other to secure the two components and maintain their positions with respect to the target site and with respect to each other. In this regard, the overlapping segments (e.g., the respective narrow-diameter portions 140, 160) may be expanded to conform with the overall diameter of the aortic wall, which may further anchor the first and second components with respect to each other and the target site, as shown in FIG. 4. For example, the tapered portions 140, 160 and smaller-diameter second ends 135, 155 may be expanded by inflating a balloon disposed within the first component 110 proximate the second end 135 (e.g., in the location of the overlapping segments). Depending on the relative sizes of the first and second components 110, 120 with respect to each (e.g., the nominal diameter of each), a certain amount of overlap may be required to ensure proper engagement between the two components. For example, in a case in which the first component 110 is oversized (e.g., sized to have a larger diameter than the second component 120) by about 4 mm, an overlap length of about 3 mm may be required to ensure that the two components, once expanded, will not move with respect to each other. In a case in which the first component 110 is not oversized or is oversized to a lesser extent, a longer overlap length may be required to ensure that the first and second components 110, 120 do not move with respect to each other once adjoined.

In some embodiments, the portion of each of the first and second components 110, 120 that forms the overlap zone (e.g., section of overlapping first and second components) may be made of a different material than the remainder of the respective component to facilitate balloon expansion. For example, whereas the non-overlapping portions of the first and second components 110, 120 may be made of a self-expanding, shape memory alloy, such as nitinol, covered by a fabric mesh, the portion configured to overlap with a corresponding portion of the other component may be made of a material such as stainless steel. In addition, as noted above, the second component 120 may be configured to have a final (expanded) diameter that is smaller than the final (expanded) diameter of the first component 110, such as approximately 4 mm to 8 mm smaller.

Moreover, by expanding the second ends 135, 155 of the respective components 110, 120 via an inflated balloon, there may be more flexibility to expand the ends to a greater or lesser degree, as appropriate, as compared to a self-expanding end. In other words, depending on the anatomy of the affected area in the particular patient, the same size endografts may be used, but expanded at the respective second ends to a greater or lesser degree as determined by the practitioner. For example, the overlap zone may be configured to be balloon expanded to a final diameter of 20 mm, 25 mm, or 30 mm, as determined to be appropriate by the surgeon. The length of the overlap zone may be adjusted, as necessary, to provide for an optimal fit between the first and second components 110, 120 to minimize leakage between the components. For example, the zone of overlap may be, in some embodiments, between approximately 2 cm and 5 cm long.

By using two components to address an area of the aorta that has a high density of arterial branches, such as the thoracoabdominal region proximate the celiac artery, SMA, and renal arteries, the arterial branches in the area may be addressed in clusters in a step-by-step manner, thereby simplifying the procedure for endovascular repair and allowing for safer, more reproducible results. In addition, using two components (e.g., a first component for the supra-renal arteries and a second component for the infra-renal arteries in this example) may allow a practitioner greater flexibility in configuring the procedure to meet the needs of the patient. For example, in some cases, a patient may only require delivery of the first component 110 to address, for example, a portion of the aorta above the celiac artery and SMA. The first component 110, in this case, may be delivered via antegrade or retrograde delivery, and extension of debranching limbs into the celiac artery and SMA may provide for an adequate "landing zone" proximate the second end 135, such that the second component 120 is not needed. In this case, the smaller-diameter second end 135 may not be expanded, and rather may be kept in a tapered configuration to allow appropriate blood flow to the renal arteries, as shown in FIG. 3. If, however, a subsequent procedure is needed for addressing the renal arteries and/or portions of the aorta near the renal arteries, a second component 120 may, at that time, be delivered to the region and mated to the first component, as described above.

Moreover, separate first and second components may allow for better sizing of one or both components to facilitate delivery into the patient's vasculature. For example, the first component 110 and/or the second component 120 may be configured to have a smaller overall diameter than a conventional endograft that is configured to address all of the celiac artery, the SMA, and the renal arteries. As a result of a smaller overall diameter, one or both components 110, 120 may be deliverable in an antegrade fashion from a supra-renal entry point, as described above, which may provide a more natural angle of access to the arteries and decrease the chances for kinking and/or fracturing the debranching limbs, either during initial delivery and deployment or later on as a result of graft migration or aortic remodeling. In addition, addressing the arterial braches in two clusters may allow a practitioner to manipulate the position of the arterial branches, for example by moving the celiac artery and SMA slightly upward and moving the renal arteries slightly downward, to provide more room between the two groups of arteries to allow for different lengths of overlap between the two components, as necessary.

Although the description above uses the example of an aortic pathology in the area of the celiac artery, SMA, and renal arteries, other conditions in other areas of the aorta may also be addressed using the described two-component, three-step procedure. For example, with reference to FIG. 5, pathologies of the ascending aorta and aortic arch may also be treated using similar components and procedures. For example, the first component 110, in this case, may be delivered in a retrograde fashion to a position proximate the innominate artery 45, with the first end 130 disposed proximate the heart and the second end 135 disposed in the aortic arch. A fenestration 190 may be provided in a tapered portion 140 and may be aligned with the innominate artery to allow the passage of a guidewire from the right subclavian artery 50 into the fenestration, such that a debranching stent-graft may be delivered over the wire and received within the fenestration 190 for support of the innominate artery. In some cases, the tapered portion 140 may extend around an entire circumference of the first component 110, as described above with respect to components configured for use in the visceral aorta. In other cases, however, the tapered portion 140 may be provided on only one side of the first component 110, such that the practitioner would need to align the tapered portion with the outer curve of the aortic arch (e.g., to correspond with the region of the aortic arch from which the innominate artery 45 and/or the left carotid artery 55 extend).

As described above, if necessary, the second component 120 may be delivered in retrograde fashion, such that a corresponding tapered portion 160 of the second component is disposed proximate the left carotid artery 55 and the left subclavian artery 60. Again, fenestrations 192, 194 may be provided in the tapered portion 160 for alignment with the left carotid artery 55 and the left subclavian artery 60. In this way, guidewires passing through the second component 120 and out through the fenestrations 192, 194 into the respective arteries may allow for debranching limbs (stent-grafts) to be delivered over the wires (e.g., from within the main endograft of the second component) for support of the left carotid artery 55 and the left subclavian artery 60. The inner surface of one or both of the first and second components 110, 120 may, as noted above, define tracks (not shown) configured to guide and support the debranching limbs out through the fenestrations and into the corresponding arterial branches.

The first and second components 110, 120 may be engaged at their respective second ends as described above via expansion of a balloon from within the overlapping second ends. In some cases, however, the second end 155 of the second component 120 may be configured to be received within the second end 135 of the first component 110, as depicted in FIG. 5, depending on the application and the governing anatomy.

In addition to the examples described above, embodiments of the invention allow for access to address pathologies in the apex of the heart via full sternotomy or mini left thoracotomy (e.g., in the fifth or sixth intercostal space). In addition, pathologies in the ascending aorta may be addressed via a partial upper sternotomy, a full sternotomy, or a mini right thoracotomy (e.g., in the third intercostal space).

The first component 110 and/or the second component 120 of the vascular assembly 100 described above may be made of any material or combination of materials that is suitable for placement in the body lumen and for occluding vascular abnormalities. For example, portions of one or both of the first and second components 110, 120, such as portions proximate the respective first ends 130, 150 of the components, may include a wire frame made of a shape memory alloy (e.g., nitinol) that is configured to self-expand from a contracted position of reduced diameter when in a constrained state (e.g., when disposed within a delivery catheter) to an expanded position when in an unconstrained state (e.g., when deployed from the delivery catheter). Other portions of one or both of the first and second components 110, 120, such as portions proximate the respective second ends 135, 155 of the components, however, may be made of metal that is not configured to self-expand, but rather can expand when an outward radial pressure is exerted from within the component (such as via an expanding balloon). In addition, portions of the wire frame may be heat treated in some cases to provide the frame with properties (e.g., a tapered shape or narrow-diameter portion, as described above) for facilitating delivery and function.

The wire frame of the first and/or second components 110, 120 may serve as a structural support for an occluding layer of material that surrounds or is embedded by the wire frame. The occluding layer may, for example, include materials such as a polymer material. As one example, for instance, the occluding layer may include polyester filaments.

Accordingly, as described above, a vascular assembly 100 is provided for treating a target site within a body lumen. The assembly 100 comprises a first component defining a first end, a second end, and a lumen extending therebetween and further comprises a second component defining a first end, a second end, and a lumen extending therebetween. As described above, the first component may be configured to engage an inner surface of a vessel wall (e.g., the wall of the aorta, such as in the visceral aorta or in the aortic arch) proximate a first group of arterial branches at the target site, and the second component may be configured to engage an inner surface of the vessel wall proximate a second group of arterial branches at the target site. For example, in the visceral aorta, the first group of arterial branches may be the celiac artery and SMA, whereas the second group of arterial branches may be the renal arteries. Similarly, in the aortic arch, the first group of arterial branches may be the innominate artery 45 and/or the right subclavian artery 50, and the second group of arterial branches may be the left carotid artery 55 and the left subclavian artery 60. Each of the first and second components may be independently deployable to the target site and may be configured for use at the target site both independently of the other component and in cooperation with the other component, as noted above.

In the embodiments depicted in FIGS. 2-5, the vascular assembly 100 includes first and second components 110, 120 in which the respective second ends 135, 155 each define a single, tubular cross-section. In other embodiments, as depicted in FIGS. 6A-10, however, the second end 235 of the first component 210 is invaginated, such that the second end 240 of the second component 220 is received within a section of the first component that is folded over onto itself, as described in greater detail below.

Accordingly, with reference to FIGS. 6A, 6B, and 7, a vascular assembly 200 may be provided that comprises a first component 210 and a second component 220. Although the first and second components 210, 220 are separate from each other for purposes of delivery and deployment at the target site, the two components are configured to cooperate and act as one device once in position within the body lumen, as illustrated in FIG. 6B. Alternatively, each component 210, 220 may be used independently of the other, as will be described in greater detail below.

In the embodiment depicted in FIGS. 6A and 6B, the first component 210 is configured (e.g., sized and shaped) to be located proximally to the heart with respect to the second component 220 and is configured such that the second component 220 is at least partially received within the first component 210. In this regard, each of the first and second components 210, 220 may have a generally tubular shape to correspond to the shape of the vessel in which they are deployed and may define a lumen to allow the flow of blood therethrough, as depicted in FIG. 7. The first component 210 may include a first end 230 and a second end 235, and the second component 220 may include a first end 240 and a second end 245. The second end 235 of the first component 210 may be configured to provide a landing zone for engaging the second end 245 of the second component 220 and holding the second component in place with respect to the first component, as shown in FIGS. 6B and 6C.

In this regard, an outer surface 231 (shown in FIG. 6A) of the first end 230 of the first component 210 may be configured to engage an inner surface of the vessel wall 250 (shown in FIG. 6C) in the area of the target site. The first end 230 may have a tubular configuration that is sized to fit snugly against the inner surface of the vessel once deployed, such that the first component 210 remains substantially in place with respect to the vessel wall 250 once installed. The first component 210 may thus, in some embodiments, comprise a shape memory alloy such as nitinol and may be configured to move between a contracted configuration when received within and radially constrained by a delivery device and an expanded configuration when deployed from the delivery device. In such embodiments, deployment of the first component 210 may allow the first end 230 of the first component 210 to be expanded to conform with the overall diameter of the vessel wall (e.g., the aortic wall in this example), which may serve to anchor the first component with respect to the target site. Although the example above describes a first component comprising a shape memory alloy, other materials compatible with the human body may be used, such as stainless steel and other metals. In such cases, the first component 210 may be expanded such that the first end 230 of the first component engages the vessel wall via balloon expansion or other expansion mechanisms.

The outer surface of the second end 235 of the first component 210, on the other hand, may be configured to engage both the inner surface of the vessel wall 250 and an outer surface of the second end 245 of the second component 220, as shown in the close-up view of FIG. 6C. In this way, the second component 220 may be at least partially received within the first component 210, and a position of the second component may be substantially fixed with respect to the first component.

With continued reference to FIGS. 6A, 6B, 6C, and 7, in some embodiments, the second end 235 of the first component 210 may include an inverted portion 260. The inverted portion 260 may be configured such that an inner surface 272 of an outer region 275 of the second end 235 faces an inner surface 278 of an inner region 280 of the second end in the inverted portion. Said differently, the second end 235 in the depicted embodiment is effectively folded back onto itself such that an outer surface 279 of the inner region 280 forms a tubular landing zone within the first component 210 for receiving and securing the second end 245 of the second component 220 (e.g., via expansion of the first end of the second component against the inner region of the inverted portion 260). In some embodiments, the length of the inner region 280 forming the landing zone may range between 1.5-5 cm long and may have an expanded inner diameter of between 2 cm and 4 cm.

Accordingly, in some embodiments, the inverted portion may form an annular space 290 between the outer region 275 and the inner region 280 of the first component 210. The outer region 275 may, in turn, define one or more fenestrations 295 that are configured to be substantially aligned with a corresponding branch vessel of the aorta. In the example depicted in FIGS. 6A-7, where the first component 210 is configured to be located proximally to the heart with respect to the second component 220, a single fenestration 295 may be provided that is configured to be substantially aligned with the innominate artery 45 (shown in FIG. 1). Moreover, the location of the fenestration 295, such as the single fenestration 295 of the first component 210 shown in FIG. 6C, may vary and, in some embodiments, may be closer or farther away from the interface between the inner region 280 and the outer region 275, as needed. In the example depicted in FIGS. 8A and 8B, however, where the first component 210 is configured to be located distally to the heart with respect to the second component 220, two fenestrations 295 may be provided in the outer region 275 of the inverted portion 260, and each fenestration may be substantially aligned with the left common carotid artery 55 or the left subclavian artery 60, respectively.

Regardless, in such embodiments, blood is able to flow into the annular space 290 and may pass through the fenestration(s) 295 such that blood flow to the respective branch vessel may be maintained. In other words, embodiments of the first component 210 are configured to provide for a landing zone for receiving the second end 245 of the second component 220 in the general area of the branch vessel, while at the same time allowing blood flow to the branch vessel to be maintained by virtue of the annular space 290 defined by the inverted portion 260. Blood flow through the first and second components is depicted in FIGS. 6B and 8B for explanatory purposes using arrows.

The inverted portion 260 of the second end 235 of the first component 210 may be formed in various ways. In some embodiments, for example, the inverted portion 260 may be made by heat setting or molding the second end 235 of the first component 210 such that the material of the first component (e.g., the shape memory alloy such as nitinol) may achieve a preset shape that defines the annular space 290. In such embodiments, the first component 210 may be delivered to the target site via a delivery catheter or other delivery device in a constrained configuration, as described above, having a reduced diameter. When the first component 210 is deployed from the delivery device, however, the first component may be allowed to self-expand such that the first end 230 of the first component engages the inner surface of the vessel wall and the second end 235 substantially attains its preset shape, including the inverted portion 260 and the annular space 290 defined thereby. In some cases, the inner region 180 of the first component 110 may be constrained in a collapsed state (e.g., disposed against the outer region 275) during deployment of the first component, such that the annular space 290 is initially collapsed. The annular space 290 may be separately expanded by the surgeon (e.g., by pulling the inner region 280 away from the outer region 275) once the first component 210 is in place within the body lumen.

The second component 220 may include a first end 240 and a second end 245. As noted above, the second end 245 may be configured to be received within the first component 210, such as via the inverted portion 260 of the second end 235 of the first component. In some cases, the second end 245 of the second component 220 may have a smaller diameter than the first end 240 when fully expanded within the first component 210, such that the second end 245 forms a tapered portion that is configured to be received within the narrower diameter of the inverted portion 260 of the first component.

In this way, the second end 245 of the second component 220 may be configured to engage and couple to the second end 235 of the first component 210 when expanded therein, while at the same time allowing for the inverted portion 260 to attain and maintain an annular space 290 for allowing blood to flow to the respective branch vessels through fenestrations in the inverted portion, as described above. In other words, the second end 245 of the second component 220 may be configured so as to apply an appropriate amount of radial force to maintain engagement with the inner region 280 of the inverted portion 260 of the first component 210, while not applying excessive radial force that may push the inner region toward the outer region 275 and collapse the annular space 290, blocking the flow of blood through the respective fenestrations.

In some embodiments, the annular space 290 may not extend all the way around the circumference of the first component 210, but rather may be localized to the area of the fenestration 295 so as to minimize the risk of clotting or turbulence of the blood flow near the interface between the inner region and the outer region of the inverted portion 260. For example, in FIG. 6D, an embodiment is depicted in which the annular space 290 is disposed in the vicinity of the fenestration 295, whereas the opposite side of the first component 291 may not include any inverted portion (e.g., may be devoid of the annular space). For example, the annular space 290 may only extend approximately 180° or less around the circumference of the second end 235 of the first component 210, as opposed to a full 360°. Accordingly, the blood may flow directly from the first component 210 into the second component 220, and the second component 220 may be configured such that the portion of the second end 245 of the second component corresponding to the straight portion 291 of the second end 235 of the first component may be devoid of any tapering or have reduced tapering as compared to the opposite side that engages with the inverted portion of the first component.

In still other embodiments, also depicted in FIG. 6D, the annular space 290 may be configured to include a support structure 292 proximate the fenestration 295. The support structure 292 may, for example, comprise a metal mesh (e.g., nitinol or stainless steel) surrounded by a Gore-tex® or Dacron® fabric webbing that, in addition to maintaining the inverted structure of the inverted portion 260, also precludes blood from flowing into portions of the annular space 290 located downstream of the fenestration 295. In this way, clotting or turbulence in the annular space 290 at or near the interface between the inner and outer regions of the inverted portion 260 may be minimized or eliminated.

Regardless of the particular configuration, the first end 240 of the second component 220 may be biased to expand radially outward (e.g., toward the vessel wall). In this regard, the first end 240 of the second component 220 may be configured to have an expanded diameter such that the first end, once deployed from the delivery device, appropriately engages the respective portion of the vessel wall to secure the second component in place with respect to the target site and/or the first component 210.

Although the description herein uses the example of a device that is configured to be delivered intravascularly for treatment of a target site in the aortic arch (e.g., in the area of the innominate artery, the left common carotid artery, and the left subclavian artery), conditions in other areas of the aorta may also be addressed using embodiments of the vascular assembly. For example, with reference to FIGS. 9 and 10, pathologies of the visceral aorta in the area of the celiac artery, SMA, and renal arteries may also be treated using similar invaginated components and procedures.

Turning now to FIGS. 9 and 10, embodiments of the vascular assembly 200 may be configured to be delivered intravascularly for treatment of a target site in other locations of the body lumen, such as in the visceral aorta. For example, with reference to FIG. 9, the first component 210 may be configured to be positioned in a location near the celiac artery 20 and SMA 25 (shown in FIG. 1), whereas the second component 220 may be configured to be positioned in a location near the renal arteries 30, 31. In the embodiment depicted in FIG. 9, the first component 210 may include an inverted portion 260 in the second end 235, and the inverted portion may form an annular space 290 as described above.

One or more fenestrations 295 may be defined in the outer region 275 of the second end 235, where each fenestration is configured to be substantially aligned with a respective branch vessel (e.g., the celiac artery or SMA) for allowing blood to flow thereto. Depending on the particular anatomy of the patient and the length of landing zone required for proper engagement of the second component 220, one of the fenestrations 295 may be defined in the area of the annular space 290, and the other fenestration may be defined outside the area of the annular space (e.g., distally from the second end 235 and the inverted portion 260, as shown). In other cases, however, such as where a relatively long landing zone is required and/or the branch vessels are more closely spaced together, both of the fenestrations 295 may be provided in the outer region 275 of the second end 235 defining the annular space 290. The second component 220, in turn, may be configured to define fenestrations 295 that are substantially aligned with the renal arteries once the two components have been deployed to the target site and are engaged with each other and the aorta.

In other embodiments, the first component 210 may be configured to be positioned distally from the heart with respect to the second component 220, as depicted in FIG. 10. Thus, in the embodiment of FIG. 10, the inverted portion 260 may define fenestrations 295 that are substantially aligned with and configured to provide blood flow to the renal arteries, whereas the second component 220 may define fenestrations that are substantially aligned with and configured to provide blood flow to the celiac artery and SMA.

Regardless of the particular configuration of the first and second components 210, 220 or their relative positions, the fenestrations 295 provided in each may be used for the extension of debranching limbs from the vascular assembly 200 into the respective branch vessels once the components are in position at the target site and/or the first and second components are engaged with each other. In some embodiments, the first component 210 and any stent-graft limbs may each be delivered separately over guidewires. Once the first component 210 and/or the second component 220 is in position proximate the target site, the debranching limbs may be extended through the fenestrations 295 and expanded into the respective arterial branches. In other embodiments, the debranching limbs may be integral to the first and/or second components 210, 220, such that the limbs and the components are delivered together.

In some embodiments, as described above and depicted with respect to the vascular assembly 100 of FIGS. 2 and 2A, tracks may be provided along an inner wall of the first component 210 for guiding stent-graft limbs along at least a portion of the length of the first component, out through the fenestrations 295, and into the aligned arterial branches. The provision of tracks through which guidewires may pass for delivering the stent-graft limbs can encourage a more natural angle for delivery of the stent-graft limbs, as noted above. In other words, by passing the stent-graft limbs through the tracks via the guidewires, the angle of the stent-graft limbs at the juncture with the wall of the first and/or second component 210, 220 may be held fixed at an angle that minimizes the stresses on the stent-graft limbs and/or the respective components. Furthermore, the tracks may serve as "landing zones" for the respective stent-graft limbs, thereby reducing the risk of migration of the stent-graft limbs with respect to the first and/or second component 210, 220. Each track may be configured to have a diameter that approximates the diameter of the branching arteries into which the tracks are configured to guide the debranching limbs. In addition, in cases where debranching limbs are not needed, plugs may be inserted into the corresponding tracks to prevent blood from escaping via the fenestrations 295.

Because blood flow is maintained to the respective branch vessels, proper positioning of the first component 210 and any debranching limbs through the fenestrations 295 may take place without raising undue concern about blood flow to the respective organs. In other words, the practitioner may take his or her time to properly position the first component 210 and any debranching limbs, for example, without significantly affecting blood flow to the patient's kidneys in the embodiment depicted in FIG. 10.

Once the first component 210 is in place, the second component 220 may be delivered to the target site by a delivery device (which may be the same as or different from the delivery device for the first component) that is inserted into the patient's vasculature. In the embodiments of FIGS. 6A and 6B (e.g., repair of a section of the aortic arch), both the first and second components 210, 220 may be delivered to the target site via a retrograde delivery (delivery against the flow of blood). In the embodiment of FIGS. 8A and 8B (e.g., repair of a section of the visceral aorta), the first component 210 may be delivered via a retrograde or an antegrade delivery (delivery in the direction of blood flow), and the second component 220 may be delivered via an antegrade delivery for engagement of the second end 245 of the second component with the second end 235 of the first component. In the embodiment shown in FIG. 9, the first component 210 may be delivered via a retrograde or an antegrade delivery, while the second component 220 may be delivered via a retrograde delivery. In the embodiment of FIG. 10, the first component 210 may be delivered via a retrograde or an antegrade delivery, while the second component 220 may be delivered via an antegrade delivery. As with the first component 210, separate or integral debranching limbs may be extended from the second component 220 through respective fenestrations 295 and into the corresponding branch arteries.

Finally, after the first and second components 210, 220 are in place, the second end 235 of the first component and the second end 245 of the second component may be connected, joined, affixed or otherwise engaged to each other to secure the two components and maintain their positions with respect to the target site and with respect to each other. In this regard, the tapered portion of the second end 245 of the second component 220 may be radially expanded to conform with the inner diameter of the first component 210 in the area of the inverted portion 260, where the corresponding portions overlap. In addition, the first end 230 of the first component 210 and the first end 240 of the second component 220 may be expanded to conform with the inner diameter of the vessel (e.g., aortic) wall, which may further anchor the first and second components with respect to each other and the target site.

In addition to the examples described above, embodiments of the invention allow for access to address pathologies in the apex of the heart via full sternotomy or mini left thoracotomy (e.g., in the fifth or sixth intercostal space). In addition, pathologies in the ascending aorta may be addressed via a partial upper sternotomy, a full sternotomy, or a mini right thoracotomy (e.g., in the third intercostal space).

By using two components to address an area of the aorta that has a high density of arterial branches, such as the aortic arch and the thoracoabdominal region proximate the celiac artery, SMA, and renal arteries, the arterial branches in the respective area may be addressed in clusters in a step-by-step manner, thereby simplifying the procedure and allowing for more reproducible results. The use of a two-component assembly as described above may further enable the surgeon to address the aortic pathologies using a procedure that does not require blood flow to any of the head vessels to be interrupted during the procedure, allowing the surgeon to perform the procedure in a more controlled manner. In addition, using two components allows a practitioner greater flexibility in configuring the procedure to meet the needs of the patient. For example, in some cases, a patient may only require delivery of the first component 110, 210 to address, for example, a portion of the aorta above the celiac artery and SMA (FIGS. 3 and 9). If, however, a subsequent procedure is needed for addressing the renal arteries and/or portions of the aorta near the renal arteries, a second component 120, 220 may, at that time, be delivered to the region and mated to the first component 110, 210, as described above.

Moreover, separate first and second components may allow for better sizing of one or both components to facilitate delivery into the patient's vasculature. For example, the first component 110, 210 and/or the second component 120, 220 may be configured to have a smaller overall diameter than a conventional endograft that is configured to address all of the branch vessels in a particular area of the aorta (such as the visceral aorta). As a result of a smaller overall diameter, one or both components 110, 210, 120, 220 may be deliverable in an antegrade fashion from a supra-renal entry point, as described above, which may provide a more natural angle of access to the arteries and decrease the chances for kinking and/or fracturing the debranching limbs, either during initial delivery and deployment or later on as a result of graft migration or aortic remodeling.

As noted above, the first component 110, 210 and/or the second component 120, 220 of the vascular assembly 100, 200 described above may be made of any material or combination of materials that is suitable for placement in the body lumen and for occluding vascular abnormalities. For example, portions of one or both of the first and second components 110, 210, 120, 220, such as portions proximate the respective first and second ends of the components, may include a wire frame made of a shape memory alloy (e.g., nitinol) that is configured to self-expand from a contracted position of reduced diameter when in a constrained state (e.g., when disposed within a delivery catheter) to an expanded position when in an unconstrained state (e.g., when deployed from the delivery catheter) to achieve a preset shape.

In other cases, however, the components or portions of the components 110, 210, 120, 220 may be made of metal that is not configured to self-expand, but rather can expand when an outward radial pressure is exerted from within the component (such as via an expanding balloon). In addition, portions of the wire frame may be heat treated in some cases to provide the frame with properties (e.g., an inverted portion and/or an annular space, as described above) for facilitating delivery and function.

The wire frame of the first and/or second components 110, 210, 120, 220 may serve as a structural support for an occluding layer of material that surrounds or is embedded by the wire frame. The occluding layer may, for example, include materials such as a polymer material. As one example, for instance, the occluding layer may include polyester filaments.

Methods for positioning a vascular assembly proximate a target site within a body lumen as described above are summarized in FIGS. 11-13. One embodiment of a method for positioning a vascular assembly proximate a target site within a body lumen is summarized in FIG. 11. The method includes providing a vascular assembly at Block 300 that includes a first component comprising a first end and a second end and a second component comprising a first end and a second end. As described above, the second end of the first component may be configured to couple to or engage the second end of the second component.

A first delivery device may be inserted into the body lumen via a supra-renal entry point, and a distal end of the first delivery device may be positioned proximate the target site. Block 310. Once in position, the first component may then be advanced toward the target site via the first delivery device and deployed from the first delivery device, such that the second end of the first component is positioned distally of at least one arterial branch (such as the celiac artery and/or the SMA) and the first end of the first component is positioned proximally of the arterial branch(es). Block 320.

After the first component is in place, if necessary to address other arterial branches, a second delivery device may be inserted into the body lumen via an infra-renal entry point, and a distal end of the second delivery device may be positioned proximate the target site. Block 330. The second component may be advanced toward the target site via the second delivery device and deployed from the delivery device, such that the second end of the second component is positioned proximate the second end of the first component (e.g., surrounding the second end of the first component, as described above). Block 340. The first component may comprise a tapered portion proximate its second end, as described above, and the tapered portion may define at least one fenestration for alignment with at least one arterial branch such that a debranching limb may be inserted through the at least one fenestration and into the at least one arterial branch. The second component may also comprise a tapered portion proximate its second end, and the tapered portion may define at least one fenestration for alignment with at least one other arterial branch such that a debranching limb may be inserted through the at least one fenestration and into the at least one other arterial branch, as described above. Furthermore, the second end of the first component may be configured to cooperate with (e.g., engage) the second end of the second component such that a position of the first and second components with respect to each other and with respect to the target site is maintained, as described above. The first and second delivery devices may be removed (e.g., withdrawn) from the body lumen after the respective components have been deployed or whenever the delivery devices are no longer needed.

According to other embodiments, a method for positioning a vascular assembly proximate a target site within a body lumen, depicted in FIG. 12, includes providing a vascular assembly at Block 400. The vascular assembly, embodiments of which are described above, may include a first component comprising a first end and a second end and a second component comprising a first end and a second end. The second end of the first component may comprise an inverted portion, such that an inner surface of an outer region of the second end faces an inner surface of an inner region of the second end in the inverted portion.

One of the first component or the second component may be delivered to the target site at Block 410. Once the component is in place, if necessary to address other arterial branches, the other of the first component or the second component may be delivered to the target site at Block 420. Each component may be delivered via the same delivery device via the same entry point into the patient's vasculature or using different delivery devices via different entry points. In any case, an outer surface of the first end of the first component may be configured to engage an inner surface of a vessel wall proximate the target site, and the second component may be at least partially received within the first component via the inverted portion of the second end of the first component. In this way, a position of the second component may be substantially fixed with respect to the first component upon engagement of the first and second components, as described above.

In still other embodiments, a method is provided for positioning a vascular assembly proximate a target site within a body lumen, as depicted in FIG. 13. The method comprises providing a vascular assembly including a first component comprising a first end and a second end and a second component comprising a first end and a second end at Block 500. A first delivery device may be inserted into the body lumen and a distal end of the first delivery device may be positioned proximate the target site at Block 510. The first component may be advanced toward the target site via the first delivery device at Block 520, and the first component may be deployed from the first delivery device at Block 530, such that the second end of the first component is positioned distally of at least one arterial branch and the first end of the first component is positioned proximally of the at least one arterial branch.

A second delivery device may be inserted into the body lumen and a distal end of the second delivery device may be positioned proximate the target site at Block 540. The second component may be advanced toward the target site via the second delivery device at Block 550, and the second component may be deployed from the delivery device at Block 560, such that the second end of the second component is positioned proximate the second end of the first component. The second end of the first component may be configured to cooperate with the second end of the second component such that a position of the first and second components with respect to each other and with respect to the target site is maintained. Furthermore, in some embodiments, the second ends of the first and second components may be engaged via balloon-expansion following deployment of the second component at Block 570 such that the second end of the second component receives the second end of the first component.

The devices and methods depicted in the figures and described above represent only certain configurations of the vascular assembly and methods of delivering the assembly. The particular configurations and methods of delivery will depend on the patient's anatomy, the condition and location of the target site, the preferences of the practitioner, and other considerations.

In summary, a vascular assembly is described above for treating a target site within a body lumen. The device includes a first component defining a first end and a second end and a second component defining a first end and a second end. The first and second components may be used independently of each other to address abnormalities of a patient's vasculature in some cases, whereas in other cases the respective second ends of the components may be engaged to form a vascular assembly as described above.

Accordingly, embodiments of the invention described herein allow for easier, more reproducible, and more anatomically correct and safer engagement of the native vessels by providing a two-component assembly that provides an internal landing zone within one of the components for receiving an end of the other component, while at the same time allowing blood flow to be maintained to branch vessels. In other words, by providing a tapered, narrower diameter portion or an inverted portion on an end of one of the components that serves as a landing zone for a corresponding end of the other component, clusters of branch vessels such as the arterial branches of the aortic arch and the visceral aorta may be kept unobstructed, and a more natural engagement of the aorta and its arterial branches may be achieved.

Moreover, either of the components in the embodiments described above can be deployed separately if needed or if the clinical situation does not allow for the completion of the procedure, while still maintaining the option to complete the intervention at a later time. This can be particularly important for addressing acute pathologies, such as acute aortic dissections, when time is of the essence, as well as chronic elective operations. In contrast, conventional devices that have a main body consisting of a single component with multiple fenestrations are more difficult to deploy at the target site and take more time to position, and the procedures for delivering such conventional devices are less efficient and pose greater risks, especially in acute settings. Safety and efficiency are significant considerations, as any elective procedure can turn into an acute procedure that would necessitate better control and a change in the pace of the procedure.

Embodiments of the two component assembly also allow for intravascular delivery via smaller diameter delivery systems. As a result, access may be available to the target site via a greater number of vessels with less likelihood of trauma to the vessel tissue, including more peripheral arteries, as well as vessels that have a smaller diameter due to disease or the smaller anatomical size of the particular patient.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. In some embodiments, certain ones of the operations above may be modified or further amplified as described below. Furthermore, in some embodiments, additional optional operations may be included, some examples of which are shown in dashed lines in FIG. 13. Modifications, additions, or amplifications to the operations above may be performed in any order and in any combination. For example, although the methods described above and in the related figures discuss positioning of the first component prior to the second component, in some cases the second component may be positioned at the target site prior to placement of the first component.

Also, as noted above, the same or different delivery devices may be used for placement of each of the first and second components, and the two components can be delivered from an antegrade pathway, a retrograde pathway, or a combination of the two (e.g., antegrade delivery of the first component and retrograde delivery of the second component). In addition, the first and second components may, in some cases, include more or fewer features than those described herein. For example, additional fenestrations may be included depending on the configuration of the arterial branches in the area to be treated and/or the anatomy of the particular patient to be treated. Although specific terms are employed herein, they are used in a generic and descriptive sense only and not for purposes of limitation.

What is claimed is:

1. A vascular assembly for treating a target site within a body lumen comprising:
    a first component defining a first end, a second end, and a lumen extending therebetween; and
    a second component defining a first end, a second end, and a lumen extending therebetween, wherein the second end of the second component is configured to receive the second end of the first component,
    wherein the first component is configured to engage an inner surface of a vessel wall proximate at least one arterial branch at the target site,
    wherein the second component is configured to engage an inner surface of the vessel wall at the target site,
    wherein each of the first and second components is independently deployable to the target site and is configured for use at the target site both independently of the other component and in cooperation with the other component, and wherein at least one of the first or second components defines at least one fenestration configured for extending a debranching limb into a corresponding arterial branch.

2. The vascular assembly of claim 1, wherein the second end of at least one of the first or second components has a smaller inner diameter than the first end of the respective component.

3. The vascular assembly of claim 1, wherein at least a portion of the first or second components is self-expandable.

4. The vascular assembly of claim 1, wherein at least one of the first or second components comprises a tapered portion proximate the respective second end.

5. The vascular assembly of claim 4, wherein the tapered portion and the respective second end are balloon-expandable.

6. The vascular assembly of claim 1, wherein the at least one of the first or second components comprises at least one track defined by an inner wall of the respective component, wherein the track is configured to receive an end of the debranching limb.

7. The vascular assembly of claim 1, wherein an outer surface of the first end of the first component is configured to engage an inner surface of a vessel wall proximate the target site, and wherein an outer surface of the second end of the first component is configured to engage an outer surface of the second component such that the second component is at least partially received within the first component and a position of the second component is substantially fixed with respect to the first component.

8. The vascular assembly of claim 1, wherein the second end of the first component comprises an inverted portion, such that an inner surface of an outer region of the second end of the first component faces an inner surface of an inner region of the second end of the first component in the inverted portion.

9. The vascular assembly of claim 8, wherein the inverted portion forms an annular space and wherein the outer region of the second end defines at least one fenestration, such that blood flowing into the annular space is able to pass through the fenestration for maintaining blood flow to a branch vessel substantially aligned with the respective fenestration.

10. The vascular assembly of claim 1, wherein the assembly is configured to be delivered intravascularly for treatment of a target site in the aortic arch.

11. The vascular assembly of claim 1, wherein the assembly is configured to be delivered intravascularly for treatment of a target site in the visceral aorta.

12. A vascular device for treating a target site within a body lumen comprising a first component defining a first end, a second end, and a lumen therebetween, wherein an outer surface of the first end is configured to engage an inner surface of a vessel wall proximate the target site, wherein an outer surface of the second end is configured to engage an outer surface of a second component such that the second component is at least partially received within the first component and a position of the second component is substantially fixed with respect to the first component, and wherein the second end of the first component comprises an inverted portion, such that an inner surface of an outer region of the second end faces an inner surface of an inner region of the second end in the inverted portion.

13. The vascular device of claim 12, wherein the inverted portion forms an annular space and wherein the outer region of the second end defines at least one fenestration, such that blood flowing into the annular space is able to pass through the fenestration for maintaining blood flow to a branch vessel substantially aligned with the respective fenestration.

14. The vascular device of claim 12, wherein the first component is configured to be located proximally to the heart with respect to the second component.

15. The vascular device of claim 12, wherein the first component is configured to be located distally to the heart with respect to the second component.

16. A vascular assembly for treating a target site within a body lumen comprising:

a first component defining a first end, a second end, and a lumen extending therebetween; and a second component defining a first end, a second end, and a lumen extending therebetween, wherein the second end of the second component is configured to receive the second end of the first component, wherein the second end of the first component comprises an inverted portion, such that an inner surface of an outer region of the second end of the first component faces an inner surface of an inner region of the second end of the first component in the inverted portion, wherein the first component is configured to engage an inner surface of a vessel wall proximate at least one arterial branch at the target site, wherein the second component is configured to engage an inner surface of the vessel wall at the target site, and wherein each of the first and second components is independently deployable to the target site and is configured for use at the target site both independently of the other component and in cooperation with the other component.

17. The vascular device of claim 16, wherein at least one of the first or second components defines at least one fenestration configured for extending a debranching limb into a corresponding arterial branch.

18. The vascular assembly of claim 17, wherein the at least one of the first or second components comprises at least one track defined by an inner wall of the respective component, wherein the track is configured to receive an end of the debranching limb.

19. The vascular assembly of claim 16, wherein at least one of the first or second components comprises a tapered portion proximate the respective second end.

20. The vascular assembly of claim 16, wherein an outer surface of the first end of the first component is configured to engage an inner surface of a vessel wall proximate the target site, and wherein an outer surface of the second end of the first component is configured to engage an outer surface of the second component such that the second component is at least partially received within the first component and a position of the second component is substantially fixed with respect to the first component.

21. The vascular assembly of claim 16, wherein the inverted portion forms an annular space and wherein the outer region of the second end defines at least one fenestration, such that blood flowing into the annular space is able to pass through the fenestration for maintaining blood flow to a branch vessel substantially aligned with the respective fenestration.

22. The vascular assembly of claim 16, wherein the assembly is configured to be delivered intravascularly for treatment of a target site in the aortic arch or the visceral aorta.

* * * * *